US007662391B2

(12) United States Patent
Murdin et al.

(10) Patent No.: US 7,662,391 B2
(45) Date of Patent: Feb. 16, 2010

(54) *CHLAMYDIA* OUTER MEMBRANE PROTEIN (OMP) AND VACCINE USES OF THE PROTEIN

(75) Inventors: Andrew D. Murdin, Richmond Hill (CA); Raymond P. Oomen, Aurora (CA); Joe Wang, Toronto (CA); Pamela Dunn, Ontario (CA)

(73) Assignee: Sanofi Pasteur Limited, Toronto, Ontario (CA)

( * ) Notice: Subject to any disclaimer, the term of this patent is extended or adjusted under 35 U.S.C. 154(b) by 296 days.

(21) Appl. No.: 11/142,306

(22) Filed: Jun. 2, 2005

(65) Prior Publication Data

US 2005/0220805 A1   Oct. 6, 2005

Related U.S. Application Data

(60) Division of application No. 10/746,251, filed on Dec. 29, 2003, now Pat. No. 7,314,869, which is a continuation of application No. 09/662,812, filed on Sep. 15, 2000, now abandoned.

(60) Provisional application No. 60/154,652, filed on Sep. 20, 1999.

(51) Int. Cl.
*A61K 39/02*   (2006.01)
(52) U.S. Cl. ............... 424/190.1; 530/350; 435/975
(58) Field of Classification Search ............... None
See application file for complete search history.

(56) References Cited

U.S. PATENT DOCUMENTS

| | | | |
|---|---|---|---|
| 6,521,745 B1 | 2/2003 | Murdin et al. | |
| 6,541,011 B2 * | 4/2003 | Punnonen et al. | 424/204.1 |
| 6,559,294 B1 * | 5/2003 | Griffais et al. | 536/23.1 |
| 6,579,854 B1 * | 6/2003 | Mitchell et al. | 514/31 |
| 6,693,087 B1 | 2/2004 | Murdin et al. | |
| 6,808,713 B1 | 10/2004 | Murdin et al. | |
| 6,822,071 B1 * | 11/2004 | Stephens et al. | 530/300 |
| 7,019,125 B2 | 3/2006 | Murdin et al. | |
| 7,070,792 B2 | 7/2006 | Murdin et al. | |
| 7,081,245 B2 | 7/2006 | Murdin et al. | |
| 2002/0082402 A1 | 6/2002 | Murdin et al. | |
| 2002/0094340 A1 | 7/2002 | Murdin et al. | |
| 2002/0094965 A1 | 7/2002 | Murdin et al. | |
| 2002/0099188 A1 | 7/2002 | Murdin et al. | |
| 2002/0132994 A1 | 9/2002 | Murdin et al. | |
| 2003/0100706 A1 | 5/2003 | Murdin et al. | |
| 2004/0254130 A1 | 12/2004 | Murdin et al. | |

FOREIGN PATENT DOCUMENTS

| | | |
|---|---|---|
| WO | WO 98/02546 A | 1/1998 |
| WO | WO 98/58953 A | 12/1998 |
| WO | 9927105 * | 6/1999 |
| WO | WO 99/27105 A | 6/1999 |
| WO | WO 99/28475 | 6/1999 |
| WO | WO 00/24765 | 5/2000 |
| WO | WO 00/27994 | 5/2000 |
| WO | WO 00/34483 | 6/2000 |
| WO | WO 00/37494 | 6/2000 |
| WO | WO 00/46359 | 8/2000 |
| WO | WO 00/66739 | 11/2000 |
| WO | WO 01/21804 A1 | 3/2001 |
| WO | WO 01/21811 A1 | 3/2001 |
| WO | WO 01/40474 A2 | 6/2001 |
| WO | WO 01/46224 A2 | 6/2001 |
| WO | WO 01/81379 A2 | 11/2001 |
| WO | WO 01/85972 A2 | 11/2001 |
| WO | WO 02/02606 A2 | 1/2002 |
| WO | WO 02/08267 A2 | 1/2002 |

OTHER PUBLICATIONS

The Dictionary of Immunology, Herbert et al eds, Academic Press, 1995.*
pp. 23-25, 27-33, Harlow et al , Antibodies A Laboratory Manual, Cold Spring Harbor Laboratory Press Inc., 1988.*
Greenbaum et al, Journal of Molecular Recognition, 20(2):75-82, 2007.*
Greenspan et al, Nature Biotechnology 17:936-937, 1999.*
Lederman et al. (Molecular Immunology 28: 1171-1181, 1991).*
Li et al. (PNAS 77: 3211-3214, 1980).*
Houghten et al. (New Approaches to Immunization, Vaccines86, Cold Spring Harbor Laboratory, p. 21-25, 1986).*
Kersten et al (Biochimica et Biophysica Acta 1241:117-138, 1995).*
Roberts et al (Infection and Immunity, 63(6):2100-2108, 1995.*
Douce et al, (Infection and Immunity, 65(7):2821-2828, 1997).*
Komase et al (Vaccine 16(⅔):248-254, 1998).*
Grayston, J. Thomas et al., "Evidence that *Chlamydia pneumoniae* Causes Pneumonia and Bronchitis", *The Journal of Infectious Diseases*, The University of Chicago Press, vol. 168, No. 5, pp. 1231-1235, (Nov. 1993).
Campos, Mauro et al., "A Chlamydial Major Outer Membrane Protein Extract as a Trachoma Vaccine Candidate",*Investigative Ophthalmology & Visual Science*, Association for Research in Vision and Ophthalmology, vol. 36, No. 8, pp. 1477-1491, (Jul. 1995).
Grayston, J. Thomas et al., "A New Respiratory Tract Pathogen: *Chlamydia pneumoniae* Strain TWAR", *The Journal of Infectious Diseases*, The University of Chicago Press, vol. 161, No. 4, pp. 618-625, (Apr. 1990).
Marrie, T. J., "Community-Acquired Pneumonia", *Clinical Infectious Diseases*, The University of Chicago Press, vol. 18, No. 4, pp. 501-669, (Apr. 1994).
Wang, S.P. et al., "Chlyamydia Infections", *Microimmunofluorescence Serological Studies with the TWAROrganism*, Cambridge University Press, pp. 329-333, (Jun. 1986).
Saikku, P. et al., "Serological Evidence of an Association of a Novel Chlyamydia, TWAR, with Chronic Coronary Heart Disease and Acute Myocardial Infarction", *The Lancet*, vol. II, No. 8618, The Lancet Ltd., pp. 983-985, (Oct. 29, 1988).

(Continued)

*Primary Examiner*—Patricia A Duffy

(57) ABSTRACT

The present invention provides vaccines and methods for immunizing a host, including humans, against disease caused by infection by a strain of *Chlamydia*, specifically *C. pneumoniae*. The vaccine and method employ an OMP (outer membrane protein) of a strain of *Chlamydia pneumoniae*. Modifications are possible within the scope of this invention.

36 Claims, 13 Drawing Sheets

OTHER PUBLICATIONS

Thom, David H. et al., "Association of Prior Infection with *Chlamydia pneumoniae* and Angiographically Demonstrated Coronary Artery Disease",*The Journal of the American Medical Association*, vol. 268, No. 1, Chlamydia pneumoniae and Coronary Artery Disease, pp. 68-72, (Jul. 1, 1992).

Linnanmaki, Eila et al., "*Chlamydia Pneumoniae*-Specific Circulating Immune Complexes in Patients with Chronic Coronary Heart Disease", *Circulation*, vol. 87, No. 4, pp. 1030-1134, (Apr. 1993).

Saikku. Pekka et al., "Chronic *Chlamydia pneumoniae* Infection as a Risk Factor for Coronary Heart Disease in the Helsinki Heart Study", *Annals of Internal Medicine*, vol. 116, No. 4, American College of Physicians, pp. 273-278, (Feb. 15, 1992).

Melnick, Sandra L.et al., "Past Infection by *Chlamydia pneumoniae* Strain TWAR and Asymptomatic Carotid Atherosclerosis", *The American Journal of Medicine*, vol. 95, pp. 499-504, (Nov. 1993).

Shor, A. et al., "Detection of *Chlamydia pneumoniae* in coronary arterial fatty streaks and atheromatous plaques", *South African Medical Journal*, vol. 82, National Center for Occupational Health, pp. 158-161, (Sep. 1992).

Kuo, Cho-chou et al., "Demonstration of *Chlamydia pneumoniae* in Atherosclerotic Lesions of Coronary Arteries", *The Journal of Infectious Diseases*, vol. 167, No. 4, The University of Chicago, pp. 841-849, (Apr. 1993).

Kuo, Cho-chuo et al., "Dection of *Chlamydia pneumoniae* in Aortic Lesions of Atherosclerosis by Immunocytochemical Stain", *Arterosclerosis and Thrombosis*, vol. 13, No. 10, pp. 1501-1504, (Oct. 1993).

Campbell, Lee Ann et al., "Detection of *Chlamydia pneumoniae* TWAR in Human Coronary Atherectomy Tissues", *The Journal of Infectious Diseases*, vol. 172, The University of Chicago, pp. 585-588, (Aug. 1995).

Chiu, B. et al., "*Chlamydia Pneumoniae*, Cytomegalovirus, and Herpes Simplex Virus in Atherosclerosis of the Carotid Artery", *Circulation*, vol. 96, No. 7, American Heart Association, pp. 2144-2148, (Oct. 7, 1997).

Ramirez, Julio A. et al., "Isolation of *Chlamydia pneumoniae* from the Coronary Artery of a Atherosclerosis", *Annals of Internal Medicine*, vol. 125, No. 12, American College of Physicians, pp. 979-982, (Dec. 15, 1996).

Jackson, Lisa A. et al., "Isolation of *Chlamydia pneumoniae* (TWAR) from a carotid atherosclerotic plaque specimen obtained by endarterectomy", *Abstracts of the 36th ICAAC*, p. 272, (Sep. 1996).

Fong, Ignatius W. et al., "Rabbit Model for *Chlamydia pneumoniae* Infection", *Journal of Clinical Microbiology*, vol. 35, No. 1, American Society of Microbiology, pp. 48-52, (Jan. 1997).

Hahn D.L. et al., "Evidence for *Chlamydia pneumoniae* Infection in steriod-dependent asthma", *Annals of Allergy Asthma & Immunology.*, vol. 80, No. 1, pp. 45-49, Jan. 1998.

Hahn, D.L. et al., "Association of *Chlamydia pneumoniae* IgA antibodies with recently simptomatic asthma", *Epidemiology Infection*, vol. 117, No. 3, Cambridge University Press, pp. 513-517, (Dec. 1996).

Bjornsson Eythor. et al., "Serology of Chlamydia in Relation to Asthma and Bronchial Hyperresponsiveness", *Scand J Infect. Dis.*, vol. 28, No. 1, Scandinavian University Press, pp. 63-69, (1996).

Hahn D.L. "Treatment of *Chlamydia pneumoniae* Infection in Adult Asthma: A Before-After Trial", *The Journal of Family Practice*, vol. 41, No. 4, Appleton & Lange, pp. 345-351, (Oct. 1995).

Allegra L. et al., "Acute exacerbations of asthma in adults: role of *Chlamydia pneumoniae* infection", *Eur Respir J.*, vol. 7, No. 12, ERS Journals Ltd., pp. 2165-2168, (Dec. 1994).

Hahn D.L. et al., "Association of *Chlamydia pneumoniae* (Strain TWAR) Infection with Wheezing, Asthmatic Bronchitis, and Adult-Onset Asthma", *The Journal of the American Medical Association*, vol. 266, No. 2, pp. 225-230, (Jul. 10, 1991).

Pal Sukumar et al., "Intranasal Immunization Induces Long-Term Protection in Mice against a *Chlamydia trachomatis* Genital Challenge", *Infection and Immunity*, vol. 64, No. 12, American Society of Microbiology,. pp. 5341-5348, (Dec. 1996).

Jones, Gareth E. et al., "Efficacy trials with tissue-culture grown, inactivated vaccines against chlamydial abortion in sheep", *Vaccine*, vol. 13, No. 8, Elsevier Science, Ltd., pp. 715-723, (1995).

Igietseme, Joseph U. et al., "Resolution of Murine Chlamydial Genital Infection by the Adoptive Transfer of a Biovar-Specific, $TH_1$ Lymphocyte Cione", *Regional Immunology*, vol. 5, John Wiley & Sons, Inc. pp. 317-324, (1993).

Magee, D. Mitchell et al., "*Chlamydia trachomatis* Pneumonia in the Severe Combined Immunodeficiency (SCID) Mouse", *Regional Immunology*, vol. 5, John Wiley & Sons, pp. 305-311, (1993).

Landers, Daniel V. et al., Role of L3T4-Bearing T-Cell Populations in Experimental Murine Chlamydial Salpingitis, *Infection and Immunity*, vol. 59, No. 10, American Society for Microbiology, pp. 3774-3777,. (Oct. 1991).

Magee, D. Mitchell et al., "Role of CD8 T Cells in Primary *Chlamydia* Infection", *Infection & Immunity*, vol. 63, No. 2, American Society for Microbiology, pp. 516-521, (Feb. 1995).

Cotter, Todd W. et al., "Protective Efficacy of Major Outer membrane Protein-Specific Immunoglobulin A (IgA) and IgG Monoclonal Antibodies in a Murine Model of *Chlamydia trachomatis* Genital Tract Infection", *Infection andImmunity*, vol. 63, No. 12, American Society for Microbiology, pp. 4704-4714, (Dec. 1995).

Campbell, Lee Ann et al.,, "Structural and Antigenic Analysis of *Chlamydia pneumoniae*", *Infection and Immunity*, vol. 58, No. 1, American Society for Microbiology, pp. 93-97, (Jan. 1990).

McCafferty, Michael C. et al., Electrophoretic Analysis of the Major Outer Membrane Protein of *Chlamydia psittaci* Reveals Multimers which are Recognized by Protective Monoclonal Antibodies, vol. 63, No. 6, American Society for Microbiology, pp. 2387-2389, (Jun. 1995).

Gaydos, Charlotte A.et al., "Similarity of *Chlamydia pneumoniae* Strains in the Variable Domain IV Region of the Major Outer Membrane Protein Gene", *Infection and Immunity*, vol. 60, No. 12, pp. 5319-5323, American Society for Microbiology, (Dec. 1992).

Wiedmann-Al-Ahmad M. et al., "Reactions of Polyclonal and Neutralizing Anti-p54 Monoclonal Antibodies with an Isolated, Species-Specific 54-Kilodalton Protein of *Chlamydia pneumoniae*", *Clinical and Diagnostic Laboratory Immunology*, vol. 4, No. 6, American Society for Microbiology, pp. 700-704, (Nov. 1997).

Hughes, Eileen E. et al., "Synthetic Peptides Representing Epitopes of Outer Membrane Protein F of *Pseudomonasaeruginosa* that Elicit Antibodies Reactive with Whole Cells of Heterologous Immunotype Strains of *P aeruginosa*", *Infection and Immunity*, vol. 60, No. 9, American Society for Microbiology, pp. 3497-3505, (Sep. 1992).

Dion, Arnold S. et al., "Virus Envelope-Based Peptide Vaccines against Virus-Induced Mammary Tumors",.*Virology*, vol. 179, No. 1, Academic Press, Inc, pp. 474-477, (1990).

Snijders, Alies et al., "Identification of linear epitopes on Semliki Forest virus E2 membrane protein and their effectiveness as a synthetic peptide vaccine", *The Journal of General Virology*, vol. 72, Part 3, Society for General Microbiology, pp. 557-565, (1991).

Langeveld, Jan P.M. et al., "Effective induction of neutralizing antibodies with the amino terminus of VP2 of canine parvovirus as a synthetic peptide", *Vaccine*, vol. 12, No. 15, pp. 1473-1480, (1994).

Kunkel et al., "Rapid and efficient site-specific mutagenesis without phenotypic selection", *Proc. Natl. Acad. USA*, vol. 82, Genetics, pp. 488-492, Jan. 1985.

Silhavy, Thomas J. et al., "Experiments with Gene Fusions", *Procedure*, vol. 46, Cold Spring Harbor Laboratory Press, pp. 191-195, (1984).

Davis, R.W. et al., "Hybridization to DNA or RNA on Solid Support", *A Manual for Genetic Engineering: Advanced Bacterial Genetics*, Cold Spring Harbor Laboratory Press, pp. 174-176, (1980).

Casey, James et al., "Rates of formation and thermal stabilities of RNA:DNA and DNA:DNA duplexes at high concentrations of formamide", *Nucleic Acids Research*, vol. 4, No. 5, Information Retrieval Limited, pp. 1539-1553, (1977).

Cagnon, Christine et al., "A new family of sugar-inducible expression vectors for *Escherichia coli*", *Protein Engineering*, vol. 4, No. 7, Oxford University Press, pp. 843-847, (1991).

Takase, Ichiro et al., "Genes Encoding Two Lipoproteins in the *leuS-dacA* Region of the *Escherichia coli* Chromosome", *Journal of Bacteriology*, vol. 169, No. 12, American Society for Microbiology, pp. 5692-5699, (Dec. 1987).

Melgosa, Mercedes P. et al., "Isolation and Characterization of a Gene Encoding a *Chlamydia pneumoniae* 76-Kilodalton Protein Containing a Species-Specific Epitope", *Infection and Immunity*, vol. 62, No. 3, American Society for Microbiology, pp. 880-886, (Mar. 1994).

Watson, Mark W. et al., "The nucleotide sequence of the 60kDa cysteine rich outer membrane protein of *Chlamydia pneumoniae* strain IOL-207", *Nucleic Acids Research*, vol. 18, No. 17, Oxford University Press,. p. 5299,.(Sep. 11, 1999).

Watson, M.W. et al., "The CrP operon of *Chlamydia psittaci* and *Chlamydia pneumoniae*", *Microbiology*, vol. 141, Society of General Microbiology, pp. 2489-2497, (1995).

Melgosa, Mercedes P. et al., "Outer membrane complex proteins of *Chlamydia pneumoniae*", *FEMS Microbiology*, vol. 112 No. 2, Elsevier, pp. 199-204, (Sep. 1, 1980).

Campbell, Lee Ann et al., "Serological Response to *Chlamydia pneumoniae* infection", *Journal of Clinical Microbiology*, vol. 28, No. 6, American Society for Microbiology, pp. 1261-1264, (Jun. 1990).

Iijima, Yoshio et al., "Chracterization of *Chlamydia pneumoniae* Species-Specific Proteins Immunodominant in Humans", *Journal of Clinical Microbiology*, vol. 32, No. 3, American Society for Microbiology, pp. 583-588,.(Mar. 1994).

http://chlamydia-www.berkeley.edu:4231/, "Chlamydia Genome Project", R&D Bioinformations, pp. 1 & 2, (Updated Sep. 23, 1999).

Bachmaier, Kurt et al., "*Chlamydia* Infections and Heart Disease Linked Through Antigenic Mimicry", *Science*, vol. 283, pp. 1335-1339, Feb. 26, 1999.

Ausubel, Frederick M. et al., "Analysis of DNA Sequences by Blotting and Hybridization: Southern Blotting", *Current Protocols in Molecular Biology*, vol. 1, John Wiley & Sons, Inc./Current Protocols, pp. 291-2915, (1993).

Allen, J.E. et al., *Eur. J. Immunology*, vol. 23, pp. 1169-1172, 1993.

Bailey, R.L. et al., *Epidemiol. Infect.*, vol. 111, pp. 314-324, 1993.

Boslego, J.W. et al., Chapter 17, Gonorrhea Vaccines, pp. 211-223, In *Vaccines and Immunotherapy*, Pergamon Press, Edited by Stanley J. Cryz. Jr., 1991.

Ellis, R.W., Ph.D., Chapter 29, pp. 568-574, In *Vaccines*, WB Saunders Company, 1988.

Stuart, E.S. et al., *Immunology*, vol. 68, pp. 469-473, 1989.

Kalman, S. et al., *Nature Genetics*, vol. 21, Apr. 1999, pp. 385-389.

Stephens, R.S. et al., *Science*, vol. 282, pp. 754-759, 1998.

Pal, S. et al., *Vaccine*, Feb. 5, 1999, vol. 17(5), pp. 459-465 (abstract only).

Penttila, T. et al., *Vaccine*, Dec. 8, 2000, vol. 19(9-10), pp. 1256-1265 (abstract only).

Igietsene, J. et al., *Microbiology &Immunology,Biodrugs*, vol. 16(1), 2002, pp. 19-35 (abstract only).

Hechard, C. et al., *Veterinary Research*, May-Jun. 2002, vol. 33(3), pp. 313-326.

Feng et al., Infection and Immunity, 64(1), pp. 363-365 (1996).

Harlow et al., Antibodies, A Laboratory Manual, Cold Spring Harbor Press, Inc., pp. 72 (1988).

Herbert et al. (Eds.), The Dictionary of Immunology, Academic Press, pp. 187.

Houghton et al., "New Approaches to Immunization", Vaccines 86, Cold Spring Harbor Laboratory, pp. 21-25 (1986).

Lederman et al., Molecular Immunology 28, pp. 1171-1181, (1991).

Li et al., PNAS 77, pp. 3211-3214, 1980.

U.S. Appl. No. 09/857,128, filed Sep. 20, 2001, Murdin et al.
U.S. Appl. No. 09/868,987, filed Dec. 23, 1999, Murdin et al.
U.S. Appl. No. 09/471,194, filed Dec. 23, 1999, Murdin et al.
U.S. Appl. No. 09/523,647, filed Mar. 10, 2000, Murdin et al.
U.S. Appl. No. 09/522,606, filed Mar. 10, 2000, Murdin et al.
U.S. Appl. No. 09/609,243, filed Jun. 30, 2000, Murdin et al.
U.S. Appl. No. 09/662,813, filed Sep. 15, 2000, Murdin et al.
U.S. Appl. No. 09/663,362, filed Sep. 15, 2000, Murdin et al.
U.S. Appl. No. 09/663,360, filed Sep. 15, 2000, Murdin et al.
U.S. Appl. No. 09/663,361, filed Sep. 15, 2000, Murdin et al.
U.S. Appl. No. 09/662,814, filed Sep. 15, 2000, Murdin et al.
U.S. Appl. No. 09/709,473, filed Nov. 13, 2000, Murdin et al.
U.S. Appl. No. 09/709,474, filed Nov. 13, 2000, Murdin et al.
U.S. Appl. No. 09/709,384, filed Nov. 13, 2000, Murdin et al.
U.S. Appl. No. 09/747,349, filed Dec. 22, 2000, Murdin et al.

Feng et al., Infection and Immunity, 64(1), pp. 363-365 (1996).

Harlow et al., Antibodies, A Laboratory Manual, Cold Spring Harbor Press, Inc., pp. 72 (1988).

Herbert et al. (Eds.), The Dictionary of Immunology, Academic Press, pp. 187, 1995.

Houghton et al., "New Approaches to Immunization", Vaccines 86, Cold Spring Harbor Laboratory, pp. 21-25 (1986).

Lederman et al., Molecular Immunology 28, pp. 1171-1181, (1991).

Li et al., PNAS 77, pp. 3211-3214, 1980.

* cited by examiner

Figure 1A. Sequence of *C. pneumoniae* OMP (outer membrane protein) gene.

```
gtggcttgat tttgaaaaag gtccatggat gtgtttataa tgttcaaggt ctccctatcc    60
aaacattgaa atacttgcta gaggagttga acatcgatct atg gga cta ttc cat    115
                                             Met Gly Leu Phe His
                                              1               5 cta act ctc ttt gga ctt tta ttg tgt agt ctt ccc att tct ctt gtt    163
Leu Thr Leu Phe Gly Leu Leu Leu Cys Ser Leu Pro Ile Ser Leu Val
                10                  15                  20 gct aaa ttc cct gag tct gta ggt cat aag atc ctt tat ata agt acg    211
Ala Lys Phe Pro Glu Ser Val Gly His Lys Ile Leu Tyr Ile Ser Thr
            25                  30                  35 caa tct aca cag cag gcc tta gca aca tat ctg gaa gct cta gat gcc    259
Gln Ser Thr Gln Gln Ala Leu Ala Thr Tyr Leu Glu Ala Leu Asp Ala
        40                  45                  50 tac ggt gat cat gac ttc ttc gtt tta aga aaa atc gga gaa gac tat    307
Tyr Gly Asp His Asp Phe Phe Val Leu Arg Lys Ile Gly Glu Asp Tyr
    55                  60                  65 ctc aag caa agc atc cac tcc tca gat ccg caa act aga aaa agc acc    355
Leu Lys Gln Ser Ile His Ser Ser Asp Pro Gln Thr Arg Lys Ser Thr
70                  75                  80                  85 atc att gga gca ggc ctg gcg gga tct tca gaa gcc ttg gac gtg ctc    403
Ile Ile Gly Ala Gly Leu Ala Gly Ser Ser Glu Ala Leu Asp Val Leu
                90                  95                 100 tcc caa gct atg gaa act gca gac ccc ctg cag cag cta ctg gtt tta    451
Ser Gln Ala Met Glu Thr Ala Asp Pro Leu Gln Gln Leu Leu Val Leu
            105                 110                 115 tcg gca gtc tca gga cat ctt ggg aaa act tct gac gac tta ctg ttt    499
Ser Ala Val Ser Gly His Leu Gly Lys Thr Ser Asp Asp Leu Leu Phe
        120                 125                 130 aaa gct tta gca tct ccc tat cct gtc atc cgc tta gaa gcc gcc tat    547
Lys Ala Leu Ala Ser Pro Tyr Pro Val Ile Arg Leu Glu Ala Ala Tyr
    135                 140                 145 aga ctt gct aat ttg aag aac act aaa gtc att gat cat cta cat tct    595
Arg Leu Ala Asn Leu Lys Asn Thr Lys Val Ile Asp His Leu His Ser
150                 155                 160                 165 ttc att cat aag ctt ccc gaa gaa atc caa tgc cta tct gcg gca ata    643
Phe Ile His Lys Leu Pro Glu Glu Ile Gln Cys Leu Ser Ala Ala Ile
                170                 175                 180
```

Figure 1B

```
ttc cta cgc ttg gag act gaa gaa tct gat gct tat att cgg gat ctc    691
Phe Leu Arg Leu Glu Thr Glu Glu Ser Asp Ala Tyr Ile Arg Asp Leu
        185                 190                 195 tta gct gcc aag aaa agc gcg att cgg agt gcc aca gct ttg cag atc    739
Leu Ala Ala Lys Lys Ser Ala Ile Arg Ser Ala Thr Ala Leu Gln Ile
            200                 205                 210 gga gaa tac caa caa aaa cgc ttt ctt ccg aca ctt agg aat ttg cta    787
Gly Glu Tyr Gln Gln Lys Arg Phe Leu Pro Thr Leu Arg Asn Leu Leu
        215                 220                 225 acg agt gcg tct cct caa gat caa gaa gct att ctt tat gct tta ggg    835
Thr Ser Ala Ser Pro Gln Asp Gln Glu Ala Ile Leu Tyr Ala Leu Gly
230                 235                 240                 245 aag ctt aag gat ggt cag agc tac tac aat ata aaa aag caa ttg cag    883
Lys Leu Lys Asp Gly Gln Ser Tyr Tyr Asn Ile Lys Lys Gln Leu Gln
                250                 255                 260 aag cct gat gtg gat gtc act tta gca gca gct caa gct tta att gct    931
Lys Pro Asp Val Asp Val Thr Leu Ala Ala Ala Gln Ala Leu Ile Ala
                265                 270                 275 ttg ggg aaa gaa gag gac gct ctt ccc gtg ata aaa aag caa gca ctt    979
Leu Gly Lys Glu Glu Asp Ala Leu Pro Val Ile Lys Lys Gln Ala Leu
        280                 285                 290 gag gag cgg cct cga gcc ctg tat gcc tta cgg cat cta ccc tct gag    1027
Glu Glu Arg Pro Arg Ala Leu Tyr Ala Leu Arg His Leu Pro Ser Glu
        295                 300                 305 ata ggg att ccg att gcc ctg ccg ata ttc cta aaa act aag aac agc    1075
Ile Gly Ile Pro Ile Ala Leu Pro Ile Phe Leu Lys Thr Lys Asn Ser
310                 315                 320                 325 gaa gcc aag ttg aat gta gct tta gct ctc tta gag tta ggg tgt gac    1123
Glu Ala Lys Leu Asn Val Ala Leu Ala Leu Leu Glu Leu Gly Cys Asp
                330                 335                 340 acc cct aaa cta ctg gaa tac att acc gaa agg ctt gtc caa cca cat    1171
Thr Pro Lys Leu Leu Glu Tyr Ile Thr Glu Arg Leu Val Gln Pro His
        345                 350                 355 tat aat gag act cta gcc ttg agt ttc tct aag ggg cgt act tta caa    1219
Tyr Asn Glu Thr Leu Ala Leu Ser Phe Ser Lys Gly Arg Thr Leu Gln
        360                 365                 370 aat tgg aag cgg gtg aac atc ata gtc cct caa gat ccc cag gag agg    1267
Asn Trp Lys Arg Val Asn Ile Ile Val Pro Gln Asp Pro Gln Glu Arg
        375                 380                 385
```

Figure 1C

```
gaa agg ttg ctc tcc aca acc cga ggt ctt gaa gag cag atc ctt acg   1315
Glu Arg Leu Leu Ser Thr Thr Arg Gly Leu Glu Glu Gln Ile Leu Thr
390                 395                 400                 405 ttt ctc ttc cgc cta cct aaa gaa gct tac ctc ccc tgt att tat aag   1363
Phe Leu Phe Arg Leu Pro Lys Glu Ala Tyr Leu Pro Cys Ile Tyr Lys
                410                 415                 420 ctt ttg gcg agt cag aaa act cag ctt gcc act act gcg att tct ttt   1411
Leu Leu Ala Ser Gln Lys Thr Gln Leu Ala Thr Thr Ala Ile Ser Phe
            425                 430                 435 tta agt cac acc tca cat cag gaa gcc tta gat cta ctt ttc caa gct   1459
Leu Ser His Thr Ser His Gln Glu Ala Leu Asp Leu Leu Phe Gln Ala
        440                 445                 450 gcg aag ctt cct gga gaa cct atc atc cgc gcc tat gca gat ctt gct   1507
Ala Lys Leu Pro Gly Glu Pro Ile Ile Arg Ala Tyr Ala Asp Leu Ala
    455                 460                 465 att tat aat ctc acc aaa gat cct gaa aaa aaa cgt tct ctc cat gat   1555
Ile Tyr Asn Leu Thr Lys Asp Pro Glu Lys Lys Arg Ser Leu His Asp
470                 475                 480                 485 tat gca aaa aag cta att cag gaa acc ttg tta ttt gtg gac acg gaa   1603
Tyr Ala Lys Lys Leu Ile Gln Glu Thr Leu Leu Phe Val Asp Thr Glu
                490                 495                 500 aac caa aga ccc cat ccc agc atg ccc tat cta cgt tat cag gtc acc   1651
Asn Gln Arg Pro His Pro Ser Met Pro Tyr Leu Arg Tyr Gln Val Thr
            505                 510                 515 cca gaa agc cgt acg aag ctc atg ttg gat att cta gag aca cta gcc   1699
Pro Glu Ser Arg Thr Lys Leu Met Leu Asp Ile Leu Glu Thr Leu Ala
        520                 525                 530 acc tcg aag tct tcc gaa gat atc cgt tta ttg ata caa ctg atg acg   1747
Thr Ser Lys Ser Ser Glu Asp Ile Arg Leu Leu Ile Gln Leu Met Thr
    535                 540                 545 gaa gga gat gca aaa aat ttc cca gtc ctt gca ggc tta ctc ata aaa   1795
Glu Gly Asp Ala Lys Asn Phe Pro Val Leu Ala Gly Leu Leu Ile Lys
550                 555                 560                 565 att gtg gag taaccccaac ctacgtctta tgaaacgttg cttcttattt           1844
Ile Val Glu ctagcttcct ttgttcttat gggttcctca gctgatgctt tgactcatca agaggctgtg 1904 aaa                                                               1907
```

Figure 2A. Restriction enzyme analysis of the *C. pneumoniae* OMP (outer membrane protein) gene.

```
                                                        CjeI
                                                        BfaI|
                                                        BseMII|
                                            MnlI           ||
                                            AciI |         ||
                                            DpnI | |       ||
                                            BstYI | | |    ||
                                            Sau3AI| | |    ||
                                            Hpy188IX| | |  ||
            MboII                DdeI  || | | |           ||
            SmlI    |            SfaNI | | | | |          ||
            BbsI |  |             AlwI|| | | | |          ||         BccI
            FokI|   | |BseRI Tth111III|| | | | |          ||         CjePI|
            ||  |   | |          ||| || | | | |           ||         ||
            AGACTATCTCAAGCAAAGCATCCACTCCTCAGATCCGCAAACTAGAAAAAGCACCATCAT
        301 ---------+---------+---------+---------+---------+---------+ 360
            TCTGATAGAGTTCGTTTCGTAGGTGAGGAGTCTAGGCGTTTGATCTTTTTCGTGGTAGTA

BsaJI
                                              StyI
                                              CviJI|
                                              CjePI ||
                                        AlwI  |    ||
                                    Hpy188IX| |    ||
                                        DpnI || |  ||
                                  BstYI |    || |  ||
                                  CjeI  |    || |  ||
                                  Sau3AI|    || |  ||
                                  AciI  |    || |  ||
                             MboII | |       || |  ||
                             MwoI| | |       || |  ||
                             ScrFI| | |      || |  ||
                           CviJI|| | |       || |  ||
                           EcoRII|| | |      || |  ||
                           HaeI || | |       || |  ||
                           HaeIII|| | |      || | ||           BsiHKAI
                           StuI  || | |      || | ||           Bsp1286I
                           Cac8I | || |      || | ||           BsaXI |          BslI
                           FauI  | || |      || | ||           Hin4I| |         PflMI
                           Eco57I| || |      || | ||           BtrI ||  |       AluI |
                           Sth132I| || |     || | ||           MaeII| || |      CviJI |         SfcI
                           ||  | || | |      || | ||           || || |          | |             |
                           TGGAGCAGGCCTGGCGGGATCTTCAGAAGCCTTGGACGTGCTCTCCCAAGCTATGGAAAC
                       361 ---------+---------+---------+---------+---------+---------+ 420
                           ACCTCGTCCGGACCGCCCTAGAAGTCTTCGGAACCTGCACGAGAGGGTTCGATACCTTTG

BbvI
                                              BsrI|
                                        BbvI  ||
                                  AlwNI |     ||
                                  AluI  |     ||
                                  CviJI |     ||
                              Fnu4HI |  |     ||
                                TseI| |  |    ||
                              PstI| | |  |    ||
                            Fnu4HI||| |  |    ||
                     PstI    CviRI|||| | |    ||          BsmAI
                     SimI    TseI ||||| | |   ||          Hpy178III
            CviRI    SfcI   ||||| | |   ||               DdeI    |        BseMII
            | |      |      |||||| | |  ||               | |              |
            TGCAGACCCCCTGCAGCAGCTACTGGTTTTATCGGCAGTCTCAGGACATCTTGGGAAAAC
        421 ---------+---------+---------+---------+---------+---------+ 480
            ACGTCTGGGGGACGTCGTCGATGACCAAAATAGCCGTCAGAGTCCTGTAGAACCCTTTTG
```

Figure 2D

```
                                        XmnI
                                        AluI|
                                        CviJI|
                                        BplI ||
                       Hpy178III          | ||
                          MnlI            | ||
                          DpnI     |      | ||                    MseI
          Hin4I       Sau3AI |     |      | ||                  AflII|
          MmeI    |  Hpy178III|    |      | ||                   SmlI|
         BseRI |  |   BsmAI  || |  |      | ||                   AluI||
        Bce83I |  |  | BsmBI || |  |      | ||                   CviJI||
         HgaI  |  |  |  SmlI || |  |      | ||                  HindIII |||
          |   ||  |  |       || |  |      | ||                      | |||
         TTTGCTAACGAGTGCGTCTCCTCAAGATCAAGAAGCTATTCTTTATGCTTTAGGGAAGCT
    781  ---------+---------+---------+---------+---------+---------+ 840
         AAACGATTGCTCACGCAGAGGAGTTCTAGTTCTTCGATAAGAAATACGAAATCCCTTCGA FokI
                  AluI |
                 CviJI |                     CviRI              Bce83I
         Hpy188IX   | |              MunI      |               MaeIII |
           BccI  |  | |              Tsp509I   |  CviJI         Tsp45I |
             |  |  | |                 |       |    |               | |
         TAAGGATGGTCAGAGCTACTACAATATAAAAAAGCAATTGCAGAAGCCTGATGTGGATGT
    841  ---------+---------+---------+---------+---------+---------+ 900
         ATTCCTACCAGTCTCGATGATGTTATATTTTTTCGTTAACGTCTTCGGACTACACCTACA MwoI
                     AceIII |
                    Tsp509I |
                       BbvI| |
                       MseI| |
                 AluI   || |
                  BbvI  || |
                  CviJI || |
            HindIII |   || |
              MwoI| |   || |
               SmlI||   || |
              AluI| ||   || |
             CviJI| ||   || |
             Fnu4HI|| ||  || |
               TseI| || ||  || |                                 BscGI
             Fnu4HI|| || ||  || |                                 EarI
              FokI| || || ||  || |                                SapI
              TseI| || || ||  || |         MnlI                   HgaI|
               || || || || ||  ||         EarI| MboII      MboII     ||
               || || || || ||  ||             |     |         |      ||
         CACTTTAGCAGCAGCTCAAGCTTTAATTGCTTTGGGGAAAGAAGAGGACGCTCTTCCCGT
    901  ---------+---------+---------+---------+---------+---------+ 960
         GTGAAATCGTCGTCGAGTTCGAAATTAACGAAACCCCTTTCTTCTCCTGCGAGAAGGGCA
```

Figure 2F

```
                                                                    ScrFI
                                                                    BsaJI  |
                                                                    EcoRII |
                                                                    MnlI   |
                                                                    DpnI   | |
                                                                    BstYI  | | |
                                                                    Sau3AI | | |
                                                          Hpy178III |   | | |
                            FauI        Bce83I              SmlI  | |   | | |
            Bce83I  Sth132I|  BsmFI        |                AlwI| | |   | | |
             RsaI  Tsp509I||   AciI|       |        HphI     | | | |    | | |
              |       |||       ||         |          |      | |  | |   | | |
            TAAGGGGCGTACTTTACAAAATTGGAAGCGGGTGAACATCATAGTCCCTCAAGATCCCCA
      1201  ---------+---------+---------+---------+---------+---------+ 1260
            ATTCCCCGCATGAAATGTTTTAACCTTCGCCCACTTGTAGTATCAGGGAGTTCTAGGGGT

MaeII
                                                              MboII|
                                       Hpy178III              MboII ||
                                         Sth132I  |      DpnI   |   ||
                                BsaJI         |   |      BstYI  |   ||
             BslI                AvaI| EarI|  |   Sau3AI |      |   ||
             BslI|                MnlI ||  SapI|  |AlwI  |      |   ||
              ||                   |   ||  ||  |   |     |      |   ||
             GGAGAGGGAAAGGTTGCTCTCCACAACCCGAGGTCTTGAAGAGCAGATCCTTACGTTTCT
      1261  ---------+---------+---------+---------+---------+---------+ 1320
             CCTCTCCCTTTCCAACGAGAGGTGTTGGGCTCCAGAACTTCTCGTCTAGGAATGCAAAGA

AluI
                                                CviJI
               EarI        AluI                HindIII  |
               EcII        CviJI                PsiI  | |     Hpy188IX
               AciI|      HindIII  |      MnlI   |    | | |   HinfI    |PleI
                ||         |   |                 |    | | |     |      |  |
             CTTCCGCCTACCTAAAGAAGCTTACCTCCCCTGTATTTATAAGCTTTTGGCGAGTCAGAA
      1321  ---------+---------+---------+---------+---------+---------+ 1380
             GAAGGCGGATGGATTTCTTCGAATGGAGGGGACATAAATATTCGAAAACCGCTCAGTCTT Cac8I                                              DdeI
                AluI  |                       MaeIII               CviJI |
                CviJI |   BseMII              Tsp45I        MnlI     |  |
                DdeI  |     MwoI              MseI  |     Hpy178III| |  |
                 |    | |    |                 |    |        ||      |  |
              AACTCAGCTTGCCACTACTGCGATTTCTTTTTTAAGTCACACCTCACATCAGGAAGCCTT
      1381  ---------+---------+---------+---------+---------+---------+ 1440
              TTGAGTCGAACGGTGATGACGCTAAAGAAAAAAATTCAGTGTGGAGTGTAGTCCTTCGGAA ScrFI
                                     FokI|
                                   EcoRII||
                                     AluI |||
                                     CviJI|||
                               HindIII  |  |||
              BbvI       Fnu4HI     |  |  |||                Bpm I     DpnI
              DpnI|       AluI|     |  |  |||               HhaI|      BglII |
             BglII ||     CviJI|    |  |  |||               ThaI ||    BstYI |
             BstYI ||     TseI|     |  |  |||     AloI  AciI  |  ||   Sau3AI |
             Sau3AI||     CjePI ||  |  |  |||   Hin4I |  CjePI|  ||CviRI |   |
              | ||          |   ||  |  |  |||    |    |   |   |  ||  |   |   |
             AGATCTACTTTTCCAAGCTGCGAAGCTTCCTGGAGAACCTATCATCCGCGCCTATGCAGA
      1441  ---------+---------+---------+---------+---------+---------+ 1500
             TCTAGATGAAAAGGTTCGACGCTTCGAAGGACCTCTTGGATAGTAGGCGCGGATACGTCT
```

Figure 2G

```
                            Hpy178III
                              DpnI    |
                         BstYI |      |          BsaXI
    BstAPI     PsiI      Sau3AI |     |   AclI    |         MslI
      MwoI    HphI |    AlwI |  |     |   MaeII   |     NlaIII|CviRI
        |       | |       |  |  |     |      |    |        ||    |
        TCTTGCTATTTATAATCTCACCAAAGATCCTGAAAAAAAACGTTCTCTCCATGATTATGC
1501    ---------+---------+---------+---------+---------+---------+ 1560
        AGAACGATAAATATTAGAGTGGTTTCTAGGACTTTTTTTTGCAAGAGAGGTACTAATACG

Hpy178III
        Tsp509I          |
         AluI  |         |
         CviJI |         |                      FokI    SimI   BccI
           | |  |                                 |       |     |
        AAAAAAGCTAATTCAGGAAACCTTGTTATTTGTGGACACGGAAAACCAAAGACCCCATCC
1561    ---------+---------+---------+---------+---------+---------+ 1620
        TTTTTTCGATTAAGTCCTTTGGAACAATAAACACCTGTGCCTTTTGGTTTCTGGGGTAGG

BcefI
        NlaIII             BstEII                 RsaI
         NspI              MaeIII                 SunI |          NlaIII
         SphI            HphI  |                 CviJI | |   AluI    |
         Cac8I |     MaeII |Tsp45I               MmeI  | | | CviJI   |
           | |         |    |  |                    |  | | |   |     |
        CAGCATGCCCTATCTACGTTATCAGGTCACCCCAGAAAGCCGTACGAAGCTCATGTTGGA
1621    ---------+---------+---------+---------+---------+---------+ 1680
        GTCGTACGGGATAGATGCAATAGTCCAGTGGGGTCTTTCGGCATGCTTCGAGTACAACCT TaqI
     Hpy178III             BbsI |
        BfaI|              MboII |
        XbaI||   CviJI      | |   Hpy188IX
     BsmAI |||     BfaI |   | |    MnlI |  EcoRV    MboII
        | |||       |    |   | |     | |    |        |
        TATTCTAGAGACACTAGCCACCTCGAAGTCTTCCGAAGATATCCGTTTATTGATACAACT
1681    ---------+---------+---------+---------+---------+---------+ 1740
        ATAAGATCTCTGTGATCGGTGGAGCTTCAGAAGGCTTCTATAGGCAAATAACTATGTTGA ApoI            CviJI
                        Tsp509I    BmrI    Cac8I |
        SfaNI           CviRI  |    BsrI|  CviRI | |   Tsp509I
          |               |    |     | |    | | |         |
        GATGACGGAAGGAGATGCAAAAAATTTCCCAGTCCTTGCAGGCTTACTCATAAAAATTGT
1741    ---------+---------+---------+---------+---------+---------+ 1800
        CTACTGCCTTCCTCTACGTTTTTTAAAGGGTCAGGAACGTCCGAATGAGTATTTTTAACA CjeI
        MaeIII                    CjePI
        Bsp24I|                   Bsp24I|           AluI
         CjePI|             AclI     ||             CviJI
         CjeI||    MaeII    MaeII    ||      BfaI   |
          ||||       |        |      ||        | |
        GGAGTAACCCCAACCTACGTCTTATGAAACGTTGCTTCTTATTTCTAGCTTCCTTTGTTC
1801    ---------+---------+---------+---------+---------+---------+ 1860
        CCTCATTGGGGTTGGATGCAGAATACTTTGCAACGAAGAATAAAGATCGAAGGAAACAAG
```

Construction of pCAmgp002

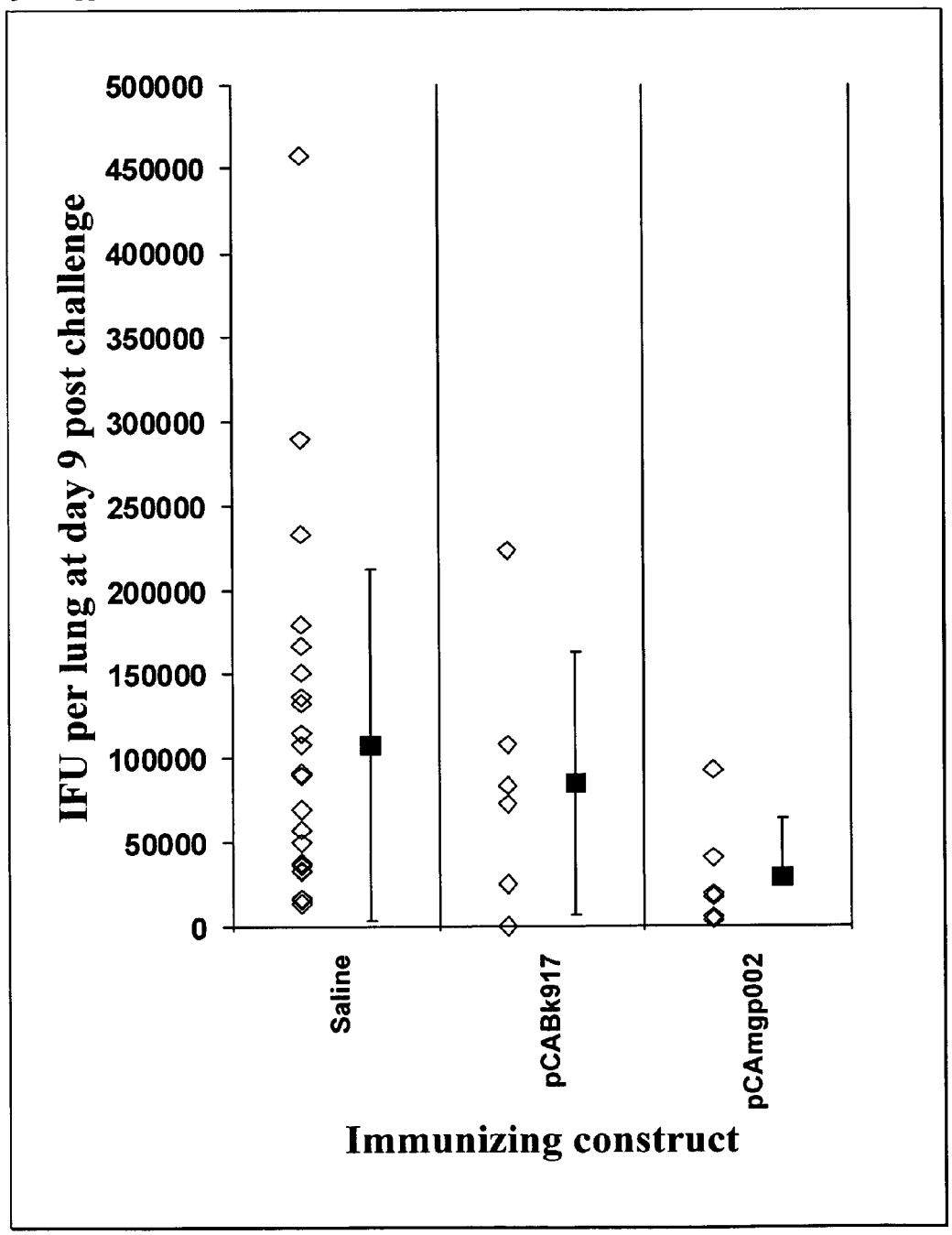
Figure 4: Protective efficacy of DNA immunization with pCAmgp002.

SEQUENCE LISTING

<160> NUMBER OF SEQ ID NOS: 4

<210> SEQ ID NO 1
<211> LENGTH: 1907
<212> TYPE: DNA
<213> ORGANISM: Chlamydia pneumoniae
<220> FEATURE:
<221> NAME/KEY: CDS
<222> LOCATION: (101)..(1804)

<400> SEQUENCE: 1

```
gtggcttgat tttgaaaaag gtccatggat gtgtttataa tgttcaaggt ctccctatcc      60
aaacattgaa atacttgcta gaggagttga acatcgatct atg gga cta ttc cat     115
                                              Met Gly Leu Phe His
                                                1               5 cta act ctc ttt gga ctt tta ttg tgt agt ctt ccc att tct ctt gtt     163
Leu Thr Leu Phe Gly Leu Leu Leu Cys Ser Leu Pro Ile Ser Leu Val
             10                  15                  20 gct aaa ttc cct gag tct gta ggt cat aag atc ctt tat ata agt acg     211
Ala Lys Phe Pro Glu Ser Val Gly His Lys Ile Leu Tyr Ile Ser Thr
         25                  30                  35 caa tct aca cag cag gcc tta gca aca tat ctg gaa gct cta gat gcc     259
Gln Ser Thr Gln Gln Ala Leu Ala Thr Tyr Leu Glu Ala Leu Asp Ala
     40                  45                  50 tac ggt gat cat gac ttc ttc gtt tta aga aaa atc gga gaa gac tat     307
Tyr Gly Asp His Asp Phe Phe Val Leu Arg Lys Ile Gly Glu Asp Tyr
 55                  60                  65 ctc aag caa agc atc cac tcc tca gat ccg caa act aga aaa agc acc     355
Leu Lys Gln Ser Ile His Ser Ser Asp Pro Gln Thr Arg Lys Ser Thr
 70                  75                  80                  85 atc att gga gca ggc ctg gcg gga tct tca gaa gcc ttg gac gtg ctc     403
Ile Ile Gly Ala Gly Leu Ala Gly Ser Ser Glu Ala Leu Asp Val Leu
             90                  95                 100 tcc caa gct atg gaa act gca gac ccc ctg cag cag cta ctg gtt tta     451
Ser Gln Ala Met Glu Thr Ala Asp Pro Leu Gln Gln Leu Leu Val Leu
        105                 110                 115 tcg gca gtc tca gga cat ctt ggg aaa act tct gac gac tta ctg ttt     499
Ser Ala Val Ser Gly His Leu Gly Lys Thr Ser Asp Asp Leu Leu Phe
        120                 125                 130 aaa gct tta gca tct ccc tat cct gtc atc cgc tta gaa gcc gcc tat     547
Lys Ala Leu Ala Ser Pro Tyr Pro Val Ile Arg Leu Glu Ala Ala Tyr
135                 140                 145 aga ctt gct aat ttg aag aac act aaa gtc att gat cat cta cat tct     595
Arg Leu Ala Asn Leu Lys Asn Thr Lys Val Ile Asp His Leu His Ser
150                 155                 160                 165 ttc att cat aag ctt ccc gaa gaa atc caa tgc cta tct gcg gca ata     643
Phe Ile His Lys Leu Pro Glu Glu Ile Gln Cys Leu Ser Ala Ala Ile
            170                 175                 180 ttc cta cgc ttg gag act gaa gaa tct gat gct tat att cgg gat ctc     691
Phe Leu Arg Leu Glu Thr Glu Glu Ser Asp Ala Tyr Ile Arg Asp Leu
        185                 190                 195 tta gct gcc aag aaa agc gcg att cgg agt gcc aca gct ttg cag atc     739
Leu Ala Ala Lys Lys Ser Ala Ile Arg Ser Ala Thr Ala Leu Gln Ile
        200                 205                 210 gga gaa tac caa caa aaa cgc ttt ctt ccg aca ctt agg aat ttg cta     787
Gly Glu Tyr Gln Gln Lys Arg Phe Leu Pro Thr Leu Arg Asn Leu Leu
215                 220                 225 acg agt gcg tct cct caa gat caa gaa gct att ctt tat gct tta ggg     835
Thr Ser Ala Ser Pro Gln Asp Gln Glu Ala Ile Leu Tyr Ala Leu Gly
```

-continued

```
             230                 235                 240                 245 aag ctt aag gat ggt cag agc tac tac aat ata aaa aag caa ttg cag          883
Lys Leu Lys Asp Gly Gln Ser Tyr Tyr Asn Ile Lys Lys Gln Leu Gln
            250                 255                 260 aag cct gat gtg gat gtc act tta gca gca gct caa gct tta att gct          931
Lys Pro Asp Val Asp Val Thr Leu Ala Ala Ala Gln Ala Leu Ile Ala
            265                 270                 275 ttg ggg aaa gaa gag gac gct ctt ccc gtg ata aaa aag caa gca ctt          979
Leu Gly Lys Glu Glu Asp Ala Leu Pro Val Ile Lys Lys Gln Ala Leu
            280                 285                 290 gag gag cgg cct cga gcc ctg tat gcc tta cgg cat cta ccc tct gag         1027
Glu Glu Arg Pro Arg Ala Leu Tyr Ala Leu Arg His Leu Pro Ser Glu
            295                 300                 305 ata ggg att ccg att gcc ctg ccg ata ttc cta aaa act aag aac agc         1075
Ile Gly Ile Pro Ile Ala Leu Pro Ile Phe Leu Lys Thr Lys Asn Ser
            310                 315                 320             325 gaa gcc aag ttg aat gta gct tta gct ctc tta gag tta ggg tgt gac         1123
Glu Ala Lys Leu Asn Val Ala Leu Ala Leu Leu Glu Leu Gly Cys Asp
                330                 335                 340 acc cct aaa cta ctg gaa tac att acc gaa agg ctt gtc caa cca cat         1171
Thr Pro Lys Leu Leu Glu Tyr Ile Thr Glu Arg Leu Val Gln Pro His
            345                 350                 355 tat aat gag act cta gcc ttg agt ttc tct aag ggg cgt act tta caa         1219
Tyr Asn Glu Thr Leu Ala Leu Ser Phe Ser Lys Gly Arg Thr Leu Gln
            360                 365                 370 aat tgg aag cgg gtg aac atc ata gtc cct caa gat ccc cag gag agg         1267
Asn Trp Lys Arg Val Asn Ile Ile Val Pro Gln Asp Pro Gln Glu Arg
    375                 380                 385 gaa agg ttg ctc tcc aca acc cga ggt ctt gaa gag cag atc ctt acg         1315
Glu Arg Leu Leu Ser Thr Thr Arg Gly Leu Glu Glu Gln Ile Leu Thr
390                 395                 400                 405 ttt ctc ttc cgc cta cct aaa gaa gct tac ctc ccc tgt att tat aag         1363
Phe Leu Phe Arg Leu Pro Lys Glu Ala Tyr Leu Pro Cys Ile Tyr Lys
            410                 415                 420 ctt ttg gcg agt cag aaa act cag ctt gcc act act gcg att tct ttt         1411
Leu Leu Ala Ser Gln Lys Thr Gln Leu Ala Thr Thr Ala Ile Ser Phe
            425                 430                 435 tta agt cac acc tca cat cag gaa gcc tta gat cta ctt ttc caa gct         1459
Leu Ser His Thr Ser His Gln Glu Ala Leu Asp Leu Leu Phe Gln Ala
            440                 445                 450 gcg aag ctt cct gga gaa cct atc atc cgc gcc tat gca gat ctt gct         1507
Ala Lys Leu Pro Gly Glu Pro Ile Ile Arg Ala Tyr Ala Asp Leu Ala
            455                 460                 465 att tat aat ctc acc aaa gat cct gaa aaa aaa cgt tct ctc cat gat         1555
Ile Tyr Asn Leu Thr Lys Asp Pro Glu Lys Lys Arg Ser Leu His Asp
470                 475                 480                 485 tat gca aaa aag cta att cag gaa acc ttg tta ttt gtg gac acg gaa         1603
Tyr Ala Lys Lys Leu Ile Gln Glu Thr Leu Leu Phe Val Asp Thr Glu
            490                 495                 500 aac caa aga ccc cat ccc agc atg ccc tat cta cgt tat cag gtc acc         1651
Asn Gln Arg Pro His Pro Ser Met Pro Tyr Leu Arg Tyr Gln Val Thr
            505                 510                 515 cca gaa agc cgt acg aag ctc atg ttg gat att cta gag aca cta gcc         1699
Pro Glu Ser Arg Thr Lys Leu Met Leu Asp Ile Leu Glu Thr Leu Ala
            520                 525                 530
```

```
acc tcg aag tct tcc gaa gat atc cgt tta ttg ata caa ctg atg acg    1747
Thr Ser Lys Ser Ser Glu Asp Ile Arg Leu Leu Ile Gln Leu Met Thr
535                 540                 545
gaa gga gat gca aaa aat ttc cca gtc ctt gca ggc tta ctc ata aaa    1795
Glu Gly Asp Ala Lys Asn Phe Pro Val Leu Ala Gly Leu Leu Ile Lys
550                 555                 560                 565 att gtg gag taaccccaac ctacgtctta tgaaacgttg cttcttattt            1844
Ile Val Glu ctagcttcct ttgttcttat gggttcctca gctgatgctt tgactcatca agaggctgtg  1904
aaa                                                                1907

<210> SEQ ID NO 2
<211> LENGTH: 568
<212> TYPE: PRT
<213> ORGANISM: Chlamydia pneumoniae

<400> SEQUENCE: 2

Met Gly Leu Phe His Leu Thr Leu Phe Gly Leu Leu Leu Cys Ser Leu
 1               5                  10                  15

Pro Ile Ser Leu Val Ala Lys Phe Pro Glu Ser Val Gly His Lys Ile
             20                  25                  30

Leu Tyr Ile Ser Thr Gln Ser Thr Gln Gln Ala Leu Ala Thr Tyr Leu
         35                  40                  45

Glu Ala Leu Asp Ala Tyr Gly Asp His Asp Phe Phe Val Leu Arg Lys
     50                  55                  60

Ile Gly Glu Asp Tyr Leu Lys Gln Ser Ile His Ser Asp Ser Pro Gln
 65                  70                  75                  80

Thr Arg Lys Ser Thr Ile Ile Gly Ala Gly Leu Ala Gly Ser Ser Glu
                 85                  90                  95

Ala Leu Asp Val Leu Ser Gln Ala Met Glu Thr Ala Asp Pro Leu Gln
            100                 105                 110

Gln Leu Leu Val Leu Ser Ala Val Ser Gly His Leu Gly Lys Thr Ser
        115                 120                 125

Asp Asp Leu Leu Phe Lys Ala Leu Ala Ser Pro Tyr Pro Val Ile Arg
130                 135                 140

Leu Glu Ala Ala Tyr Arg Leu Ala Asn Leu Lys Asn Thr Lys Val Ile
145                 150                 155                 160

Asp His Leu His Ser Phe Ile His Lys Leu Pro Glu Glu Ile Gln Cys
                165                 170                 175

Leu Ser Ala Ala Ile Phe Leu Arg Leu Glu Thr Glu Glu Ser Asp Ala
            180                 185                 190

Tyr Ile Arg Asp Leu Leu Ala Ala Lys Lys Ser Ala Ile Arg Ser Ala
        195                 200                 205

Thr Ala Leu Gln Ile Gly Glu Tyr Gln Gln Lys Arg Phe Leu Pro Thr
    210                 215                 220

Leu Arg Asn Leu Leu Thr Ser Ala Ser Pro Gln Asp Gln Glu Ala Ile
225                 230                 235                 240

Leu Tyr Ala Leu Gly Lys Leu Lys Asp Gly Gln Ser Tyr Tyr Asn Ile
                245                 250                 255

Lys Lys Gln Leu Gln Lys Pro Asp Val Asp Val Thr Leu Ala Ala Ala
            260                 265                 270

Gln Ala Leu Ile Ala Leu Gly Lys Glu Glu Asp Ala Leu Pro Val Ile
        275                 280                 285

Lys Lys Gln Ala Leu Glu Glu Arg Pro Arg Ala Leu Tyr Ala Leu Arg
    290                 295                 300
```

```
His Leu Pro Ser Glu Ile Gly Ile Pro Ile Ala Leu Pro Ile Phe Leu
305                 310                 315                 320

Lys Thr Lys Asn Ser Glu Ala Lys Leu Asn Val Ala Leu Ala Leu Leu
                325                 330                 335

Glu Leu Gly Cys Asp Thr Pro Lys Leu Leu Glu Tyr Ile Thr Glu Arg
            340                 345                 350

Leu Val Gln Pro His Tyr Asn Glu Thr Leu Ala Leu Ser Phe Ser Lys
        355                 360                 365

Gly Arg Thr Leu Gln Asn Trp Lys Arg Val Asn Ile Ile Val Pro Gln
    370                 375                 380

Asp Pro Gln Glu Arg Glu Arg Leu Leu Ser Thr Thr Arg Gly Leu Glu
385                 390                 395                 400

Glu Gln Ile Leu Thr Phe Leu Phe Arg Leu Pro Lys Glu Ala Tyr Leu
                405                 410                 415

Pro Cys Ile Tyr Lys Leu Leu Ala Ser Gln Lys Thr Gln Leu Ala Thr
            420                 425                 430

Thr Ala Ile Ser Phe Leu Ser His Thr Ser His Gln Glu Ala Leu Asp
        435                 440                 445

Leu Leu Phe Gln Ala Ala Lys Leu Pro Gly Glu Pro Ile Ile Arg Ala
    450                 455                 460

Tyr Ala Asp Leu Ala Ile Tyr Asn Leu Thr Lys Asp Pro Glu Lys Lys
465                 470                 475                 480

Arg Ser Leu His Asp Tyr Ala Lys Lys Leu Ile Gln Glu Thr Leu Leu
                485                 490                 495

Phe Val Asp Thr Glu Asn Gln Arg Pro His Pro Ser Met Pro Tyr Leu
            500                 505                 510

Arg Tyr Gln Val Thr Pro Glu Ser Arg Thr Lys Leu Met Leu Asp Ile
        515                 520                 525

Leu Glu Thr Leu Ala Thr Ser Lys Ser Ser Glu Asp Ile Arg Leu Leu
    530                 535                 540

Ile Gln Leu Met Thr Glu Gly Asp Ala Lys Asn Phe Pro Val Leu Ala
545                 550                 555                 560

Gly Leu Leu Ile Lys Ile Val Glu
                565

<210> SEQ ID NO 3
<211> LENGTH: 44
<212> TYPE: DNA
<213> ORGANISM: Artificial Sequence
<220> FEATURE:
<223> OTHER INFORMATION: 5' PCR primer

<400> SEQUENCE: 3
ataagaatgc ggccgccacc atgggactat tccatctaac tctc            44

<210> SEQ ID NO 4
<211> LENGTH: 36
<212> TYPE: DNA
<213> ORGANISM: Artificial Sequence
<220> FEATURE:
<223> OTHER INFORMATION: 3' PCR primer

<400> SEQUENCE: 4
gcgccggatc ccctccacaa ttttatgag taagcc                       36
```

CHLAMYDIA OUTER MEMBRANE PROTEIN (OMP) AND VACCINE USES OF THE PROTEIN

REFERENCE TO RELATED APPLICATIONS

This is a divisional application of U.S. patent application Ser. No. 10/746,251, filed Dec. 29, 2003, now U.S. Pat. No. 7,314,869, which is a continuation of U.S. patent application Ser. No. 09/662,812 filed Sep. 15, 2000, now abandoned, which claims the benefit of U.S. Provisional Application No. 60/154,652, filed Sep. 20, 1999, the content of which is herein incorporated by reference.

FIELD OF INVENTION

The present invention relates to the *Chlamydia* OMP (outer membrane protein) antigen and corresponding DNA molecules, which can be used to prevent and treat *Chlamydia* infection in mammals, such as humans.

BACKGROUND OF THE INVENTION

Chlamydiae are prokaryotes. They exhibit morphologic and structural similarities to gram-negative bacteria including a trilaminar outer membrane, which contains lipopolysaccharide and several membrane proteins that are structurally and functionally analogous to proteins found in *E coli*. They are obligate intra-cellular parasites with a unique biphasic life cycle consisting of a metabolically inactive but infectious extracellular stage and a replicating but non-infectious intracellular stage. The replicative stage of the life-cycle takes place within a membrane-bound inclusion which sequesters the bacteria away from the cytoplasm of the infected host cell.

*C. pneumoniae* is a common human pathogen, originally described as the TWAR strain of *Chlamydia psittaci* but subsequently recognised to be a new species. *C. pneumoniae* is antigenically, genetically and morphologically distinct from other chlamydia species (*C. trachomatis, C. pecorum* and *C. psittaci*). It shows 10% or less DNA sequence homology with either of *C. trachomatis* or *C. psittaci*.

*C. pneumoniae* is a common cause of community acquired pneumonia, only less frequent than *Streptococcus pneumoniae* and *Mycoplasma pneumoniae* (Grayston et al. (1995) Journal of Infectious Diseases 168:1231; Campos et al. (1995) Investigation of Ophthalmology and Visual Science 36:1477). It can also cause upper respiratory tract symptoms and disease, including bronchitis and sinusitis (Grayston et al. (1995) Journal of Infectious Diseases 168:1231; Grayston et al (1990) Journal of Infectious Diseases 161:618; Marrie (1993) Clinical Infectious Diseases. 18:501; Wang et al (1986) Chlamydial infections Cambridge University Press, Cambridge. p. 329. The great majority of the adult population (over 60%) has antibodies to *C. pneumoniae* (Wang et al (1986) Chlamydial infections. Cambridge University Press, Cambridge. p. 329), indicating past infection which was unrecognized or asymptomatic.

*C. pneumoniae* infection usually presents as an acute respiratory disease (i.e., cough, sore throat, hoarseness, and fever; abnormal chest sounds on auscultation). For most patients, the cough persists for 2 to 6 weeks, and recovery is slow. In approximately 10% of these cases, upper respiratory tract infection is followed by bronchitis or pneumonia. Furthermore, during a *C. pneumoniae* epidemic, subsequent co-infection with pneumococcus has been noted in about half of these pneumonia patients, particularly in the infirm and the elderly. As noted above, there is more and more evidence that *C. pneumoniae* infection is also linked to diseases other than respiratory infections.

The reservoir for the organism is presumably people. In contrast to *C. psittaci* infections, there is no known bird or animal reservoir. Transmission has not been clearly defined. It may result from direct contact with secretions, from fomites, or from airborne spread. There is a long incubation period, which may last for many months. Based on analysis of epidemics, *C. pneumoniae* appears to spread slowly through a population (case-to-case interval averaging 30 days) because infected persons are inefficient transmitters of the organism. Susceptibility to *C. pneumoniae* is universal. Reinfections occur during adulthood, following the primary infection as a child. *C. pneumoniae* appears to be an endemic disease throughout the world, noteworthy for superimposed intervals of increased incidence (epidemics) that persist for 2 to 3 years. *C. trachomatis* infection does not confer cross-immunity to *C. pneumoniae*. Infections are easily treated with oral antibiotics, tetracycline or erythromycin (2 g/d, for at least 10 to 14 d). A recently developed drug, azithromycin, is highly effective as a single-dose therapy against chlamydial infections.

In most instances, *C. pneumoniae* infection is often mild and without complications, and up to 90% of infections are subacute or unrecognized. Among children in industrialized countries, infections have been thought to be rare up to the age of 5 y, although a recent study (E Normann et al, *Chlamydia pneumoniae* in children with acute respiratory tract infections, Acta Paediatrica, 1998, Vol 87, Iss 1, pp 23-27) has reported that many children in this age group show PCR evidence of infection despite being seronegative, and estimates a prevalence of 17-19% in 2-4 y olds. In developing countries, the seroprevalence of *C. pneumoniae* antibodies among young children is elevated, and there are suspicions that *C. pneumoniae* may be an important cause of acute lower respiratory tract disease and mortality for infants and children in tropical regions of the world.

From seroprevalence studies and studies of local epidemics, the initial *C. pneumoniae* infection usually happens between the ages of 5 and 20 y. In the USA, for example, there are estimated to be 30,000 cases of childhood pneumonia each year caused by *C. pneumoniae*. Infections may cluster among groups of children or young adults (e.g., school pupils or military conscripts).

*C. pneumoniae* causes 10 to 25% of community-acquired lower respiratory tract infections (as reported from Sweden, Italy, Finland, and the USA). During an epidemic, *C. pneumonia* infection may account for 50 to 60% of the cases of pneumonia. During these periods, also, more episodes of mixed infections with *S. pneumoniae* have been reported.

Reinfection during adulthood is common; the clinical presentation tends to be milder. Based on population seroprevalence studies, there tends to be increased exposure with age, which is particularly evident among men. Some investigators have speculated that a persistent, asymptomatic *C. pneumoniae* infection state is common.

In adults of middle age or older, *C. pneumoniae* infection may progress to chronic bronchitis and sinusitis. A study in the USA revealed that the incidence of pneumonia caused by *C. pneumoniae* in persons younger than 60 years is 1 case per 1,000 persons per year; but in the elderly, the disease incidence rose three-fold. *C. pneumoniae* infection rarely leads to hospitalization, except in patients with an underlying illness.

Of considerable importance is the association of atherosclerosis and *C. pneumoniae* infection. There are several epidemiological studies showing a correlation of previous infections with *C. pneumoniae* and heart attacks, coronary artery and carotid artery disease (Saikku et al. (1988) Lancet;ii:983; Thom et al. (1992) JAMA 268:68; Linnanmaki et al. (1993), Circulation 87:1030; Saikku et al. (1992) Annals Internal Medicine 116:273; Melnick et al (1993) American Journal of Medicine 95:499). Moreover, the organisms has been detected in atheromas and fatty streaks of the coronary, carotid, peripheral arteries and aorta (Shor et al. (1992) South African. Medical Journal 82:158; Kuo et al. (1993) Journal of Infectious Diseases 167:841; Kuo et al. (1993) Arteriosclerosis and Thrombosis 13:1500; Campbell et al (1995) Journal of Infectious Diseases 172:585; Chiu et al. Circulation, 1997 (In Press)). Viable *C. pneumoniae* has been recovered from the coronary and carotid artery (Ramirez et al (1996) Annals of Internal Medicine 125:979; Jackson et al. Abst. K121, p272, 36th ICAAC, 15-18 September 1996, New Orleans). Furthermore, it has been shown that *C. pneumoniae* can induce changes of atherosclerosis in a rabbit model (Fong et al (1997) Journal of Clinical Microbiolology 35:48). Taken together, these results indicate that it is highly probable that *C. pneumoniae* can cause atherosclerosis in humans, though the epidemiological importance of chlamydial atherosclerosis remains to be demonstrated.

A number of recent studies have also indicated an association between *C. pneumoniae* infection and asthma. Infection has been linked to wheezing, asthmatic bronchitis, adult-onset asthma and acute exacerbations of asthma in adults, and small-scale studies have shown that prolonged antibiotic treatment was effective at greatly reducing the severity of the disease in some individuals (Hahn D L, et al. Evidence for *Chlamydia pneumoniae* infection in steroid-dependent asthma. Ann Allergy Asthma Immunol. 1998 January; 80(1): 45-49; Hahn D L, et al. Association of *Chlamydia pneumoniae* IgA antibodies with recently symptomatic asthma. Epidemiol Infect. 1996 December; 117(3): 513-517; Bjornsson E, et al. Serology of chlamydia in relation to asthma and bronchial hyperresponsiveness. Scand J Infect Dis. 1996; 28(1): 63-69; Hahn D L. Treatment of *Chlamydia pneumoniae* infection in adult asthma: a before-after trial. J Fam Pract. 1995 October; 41(4): 345-351; Allegra L, et al. Acute exacerbations of asthma in adults: role of *Chlamydia pneumoniae* infection. Eur Respir J. 1994 December; 7(12): 2165-2168; Hahn D L, et al. Association of *Chlamydia pneumoniae* (strain TWAR) infection with wheezing, asthmatic bronchitis, and adult-onset asthma. JAMA. 1991 Jul. 10; 266(2): 225-230).

In light of these results a protective vaccine against *C. pneumoniae* infection would be of considerable importance. There is not yet an effective vaccine for any human chlamydial infection. It is conceivable that an effective vaccine can be developed using physically or chemically inactivated Chlamydiae. However, such a vaccine does not have a high margin of safety. In general, safer vaccines are made by genetically manipulating the organism by attenuation or by recombinant means. Accordingly, a major obstacle in creating an effective and safe vaccine against human chlamydial infection has been the paucity of genetic information regarding *Chlamydia*, specifically *C. pneumoniae*.

Studies with *C. trachomatis* and *C. psittaci* indicate that safe and effective vaccine against *Chlamydia* is an attainable goal. For example, mice which have recovered from a lung infection with *C. trachomatis* are protected from infertility induced by a subsequent vaginal challenge (Pal et al. (1996) Infection and Immunity.64:5341). Similarly, sheep immunized with inactivated *C. psittaci* were protected from subsequent chlamydial-induced abortions and stillbirths (Jones et al. (1995) Vaccine 13:715). Protection from chlamydial infections has been associated with Th1 immune responses, particularly the induction of INFg—producing CD4+ T-cells (Igietsemes et al. (1993) Immunology 5:317). The adoptive transfer of CD4+ cell lines or clones to nude or SCID mice conferred protection from challenge or cleared chronic disease (Igietseme et al (1993) Regional Immunology 5:317; Magee et al (1993) Regional Immunology 5: 305), and in vivo depletion of CD4+ T cells exacerbated disease post-challenge (Landers et al (1991) Infection & Immunity 59:3774; Magee et al (1995) Infection & Immunity 63:516). However, the presence of sufficiently high titres of neutralising antibody at mucosal surfaces can also exert a protective effect (Cotter et al. (1995) Infection and Immunity 63:4704).

Antigenic variation within the species *C. pneumoniae* is not well documented due to insufficient genetic information, though variation is expected to exist based on *C. trachomatis*. Serovars of *C. trachomatis* are defined on the basis of antigenic variation in the major outer membrane protein (MOMP), but published *C. pneumoniae* MOMP gene sequences show no variation between several diverse isolates of the organism (Campbell et al. Infection and Immunity (1990) 58:93; McCafferty et al Infection and Immunity (1995) 63:2387-9; Gaydos et al. Infection and Immunity. (1992) 60(12):5319-5323). The gene encoding a 76 kDa antigen has been cloned from a single strain of *C. pneumoniae* and the sequence published (Perez Melgosa et al. Infection and Immunity.(1994) 62:880). An operon encoding the 9 kDa and 60 kDa cysteine-rich outer membrane protein genes has been described (Watson et al., Nucleic Acids Res (1990) 18:5299; Watson et al., Microbiology (1995) 141:2489). Many antigens recognized by immune sera to *C. pneumoniae* are conserved across all chlamydiae, but 98 kDa, 76 kDa and several other proteins may be *C. pneumoniae*-specific (Perez Melgosa et al. Infection and Immunity.(1994) 62:880; Melgosa et al., FEMS Microbiol Lett (1993) 112 :199; Campbell et al., J Clin Microbiol (1990) 28 :1261; Iijima et al., J Clin Microbiol (1994) 32:583). An assessment of the number and relative frequency of any *C. pneumoniae* serotypes, and the defining antigens, is not yet possible. The entire genome sequence of *C. pneumoniae* strain CWL-029 is now known and as further sequences become available a better understanding of antigenic variation may be gained.

Many antigens recognised by immune sera to *C. pneumoniae* are conserved across all chlamydiae, but 98 kDa, 76 kDa and 54 kDa proteins appear to be *C. pneumoniae*-specific (Campos et al. (1995) Investigation of Ophthalmology and Visual Science 36:1477; Marrie (1993) Clinical Infectious Diseases. 18:501; Wiedmann-Al-Ahmad M, et al. Reactions of polyclonal and neutralizing anti-p54 monoclonal antibodies with an isolated, species-specific 54-kilodalton protein of *Chlamydia pneumoniae*. Clin Diagn Lab Immunol. 1997 November; 4(6): 700-704).

Immunoblotting of isolates with sera from patients does show variation of blotting patterns between isolates, indicating that serotypes *C. pneumoniae* may exist (Grayston et al. (1995) Journal of Infectious Diseases 168:1231; Ramirez et al (1996) Annals of Internal Medicine 125:979). However, the results are potentially confounded by the infection status of the patients, since immunoblot profiles of a patient's sera change with time post-infection. An assessment of the number and relative frequency of any serotypes, and the defining antigens, is not yet possible.

Accordingly, a need exists for identifying and isolating polynucleotide sequences of *C. pneumoniae* for use in preventing and treating *Chlamydia* infection.

SUMMARY OF THE INVENTION

The present invention provides purified and isolated polynucleotide molecules that encode the *Chlamydia* polypeptides designated OMP (outer membrane protein) (SEQ ID No: 1) which can be used in methods to prevent, treat, and diagnose *Chlamydia* infection. In one form of the invention, the polynucleotide molecules are DNA that encode the polypeptide of SEQ ID No: 2.

Another form of the invention provides polypeptides corresponding to the isolated DNA molecules. The amino acid sequence of the corresponding encoded polypeptide is shown as SEQ ID No: 2.

Those skilled in the art will readily understand that the invention, having provided the polynucleotide sequences encoding the *Chlamydia* OMP (outer membrane protein) protein, also provides polynucleotides encoding fragments derived from such a polypeptide. Moreover, the invention is understood to provide mutants and derivatives of such polypeptides and fragments derived therefrom, which result from the addition, deletion, or substitution of non-essential amino acids as described herein. Those skilled in the art would also readily understand that the invention, having provided the polynucleotide sequences encoding *Chlamydia* polypeptides, further provides monospecific antibodies that specifically bind to such polypeptides.

The present invention has wide application and includes expression cassettes, vectors, and cells transformed or transfected with the polynucleotides of the invention. Accordingly, the present invention further provides (i) a method for producing a polypeptide of the invention in a recombinant host system and related expression cassettes, vectors, and transformed or transfected cells; (ii) a vaccine, or a live vaccine vector such as a pox virus, *Salmonella typhimurium*, or *Vibrio cholerae* vector, containing a polynucleotide of the invention, such vaccines and vaccine vectors being useful for, e.g., preventing and treating *Chlamydia* infection, in combination with a diluent or carrier, and related pharmaceutical compositions and associated therapeutic and/or prophylactic methods; (iii) a therapeutic and/or prophylactic use of an RNA or DNA molecule of the invention, either in a naked form or formulated with a delivery vehicle, a polypeptide or combination of polypeptides, or a monospecific antibody of the invention, and related pharmaceutical compositions; (iv) a method for diagnosing the presence of *Chlamydia* in a biological sample, which can involve the use of a DNA or RNA molecule, a monospecific antibody, or a polypeptide of the invention; and (v) a method for purifying a polypeptide of the invention by antibody-based affinity chromatography.

In one aspect, there is described a vaccine composition comprising a protein and a compound, wherein the protein comprises the amino acid sequence set forth in SEQ ID NO:2, and wherein the compound facilitates delivery and/or enhance an immune response to the part of the protein having the amino acid sequence set forth in SEQ ID NO:2.

In another aspect, there is described the composition outlined above, wherein the protein is a fusion protein comprising the amino acid sequence set forth in SEQ ID NO:2 fused with a heterologous polypeptide. The heterologous polypeptide may be a peptide tail for purifying the protein.

In another aspect, there is described the compositions outlined above, wherein the compound is a liposome. The liposome may be at least one liposome selected from the group consisting of neutral liposomes, anionic liposomes, microspheres, ISCOMS, and virus-like-particles (VLPs).

In another aspect, there is described the compositions outlined above, wherein the compound is an adjuvant. The adjuvant may be at least one adjuvant selected from the group consisting of an aluminum compound such as aluminum hydroxide, aluminum phosphate, or aluminum hydroxy phosphate, RIBI, polyphosphazene, DC-chol (3b-(N—(N',N'-dimethyl aminomethane)-carbamoyl) cholesterol and QS-21.

In another aspect, there is described the compositions outlined above, which is suitable for parenteral administration, or for mucosal administration. In compositions suitable for mucosal administration, the adjuvant may be at least one adjuvant selected from the group consisting of bacterial toxin, bacterial monophosphoryl lipid A (MPLA) (such as MPLA of *E. coli*, *Salmonella minnesota*, *Salmonella typhimurium*, or *Shigella flexneri*), saponin, polylactide glycolide (PLGA) microsphere, polyphosphazene, DC-chol (3b-(N—(N',N'-dimethyl aminomethane)-carbamoyl) cholesterol, and QS-21. The bacterial toxin may be selected from the group consisting of cholera toxin (CT), *E. coli* heat-labile toxin (LT), *Clostridium difficile* toxin A, *pertussis* toxin (PT), and combinations, subunits, toxoids, or mutants thereof that retain adjuvant activity and/or have reduced toxicity. Specifically, the adjuvant may be at least one bacterial toxin selected from the group consisting of native cholera toxin subunit B (CTB), Arg-7-Lys CT mutant, Arg-192-Gly LT mutant, Arg-9-Lys PT mutant, Glu-129-Gly PT mutant, Ser-63-Lys LT mutant, Ala-69-Gly LT mutant, Glu-110-Asp LT mutant, and Glu-112-Asp LT mutant.

In another aspect, there is described the compositions outlined above, in unit dosage form.

In another aspect, there is described the compositions outlined above, further comprising an additional *Chlamydia* polypeptide that enhances an immune response to the part of the protein having the amino acid sequence set forth in SEQ ID NO:2.

In another aspect, there is described a vaccine composition comprising a protein fused to a heterologous polypeptide having adjuvant activity, wherein the protein comprises the amino acid sequence set forth in SEQ ID NO:2. The heterologous polypeptide having adjuvant activity may be suitable as an adjuvant for parenteral administration, or as an adjuvant for mucosal administration. Specifically, the heterologous polypeptide may be subunit B of cholera toxin (CTB) or subunit B of *E. coli* heat-labile toxin (LTB). The heterologous polypeptide may also be a strong T-cell epitope and/or a strong B-cell epitope such as a strong T-cell epitope and/or a strong B-cell epitope from hepatitis B virus core antigen.

In another aspect, there is described a method for treating or preventing a *Chlamydia* infection, the method comprising the step of administering to a subject the vaccine composition as outlined above. The method may further comprise the step of administering to the subject an antibiotic (such as a macrolide, a tetracycline, or a derivative thereof, or azithromycin or doxicyclin), an antacid, sucralfate, a cytokine immunomodulator (such as interleukin-2 (IL-2), interleukin-12 (IL-12), or a steroid) or a combination thereof.

In another aspect, there is described a vaccination kit comprising the vaccine composition as outlined above and instructions for its use in vaccinating a subject against *Chlamydia* infection.

BRIEF DESCRIPTION OF THE DRAWINGS

The present invention will be further understood from the following description with reference to the drawings, in which:

FIG. 1 shows the nucleotide sequence of the OMP (outer membrane protein) gene (SEQ ID No: 1) and the deduced amino acid sequence of OMP (outer membrane protein) from *Chlamydia pneumoniae* (SEQ ID No: 2).

FIG. 4 illustrates protection against *C. pneumoniae* infection by pCAmgp002 following DNA immunization.

DETAILED DESCRIPTION OF INVENTION

Figure 2C:
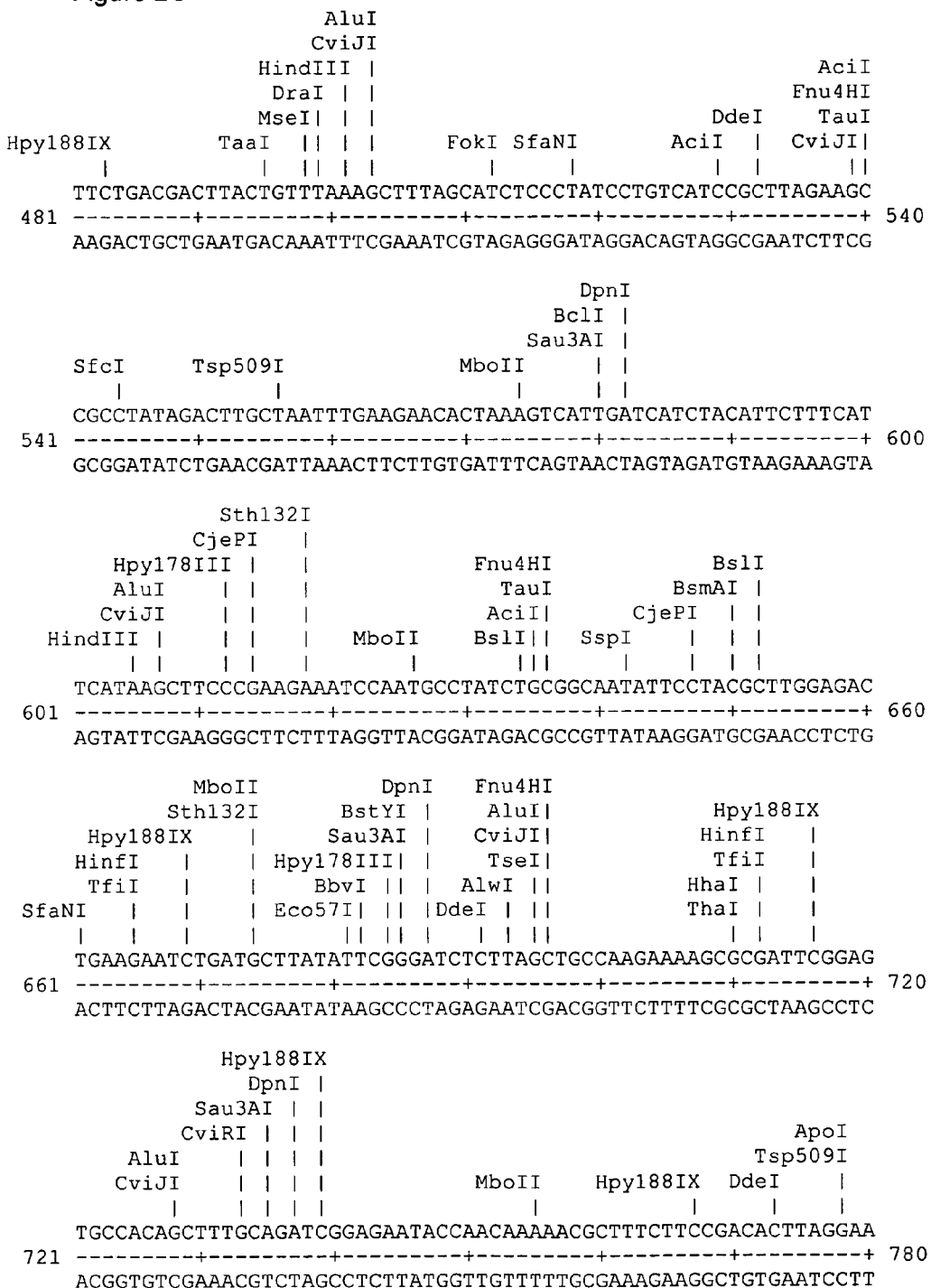
FIG. 2 shows the restriction enzyme analysis of the *C. pneumoniae* OMP (outer membrane protein) gene (SEQ ID No: 1).
Figure 2E:
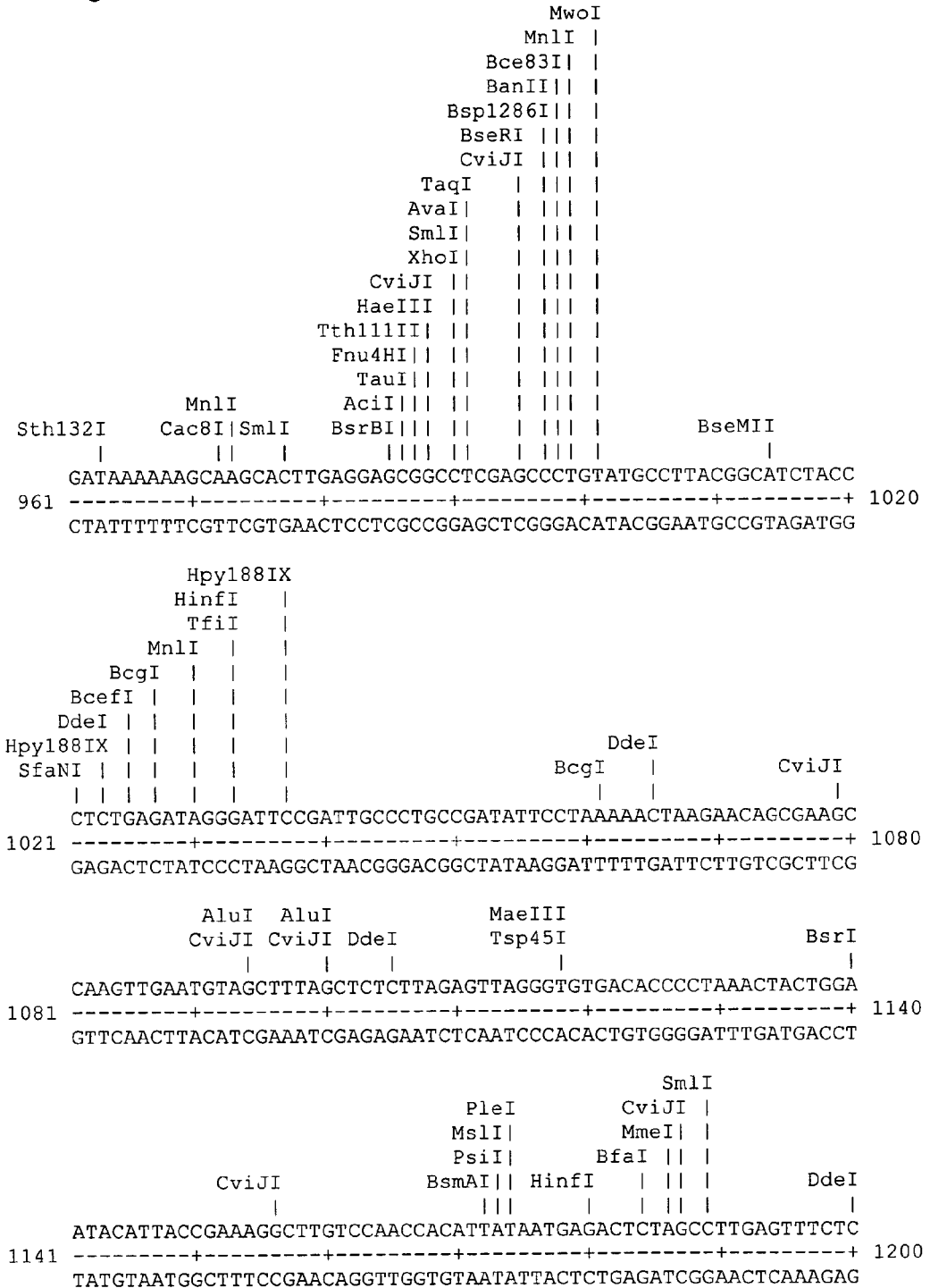
Figure 2H:
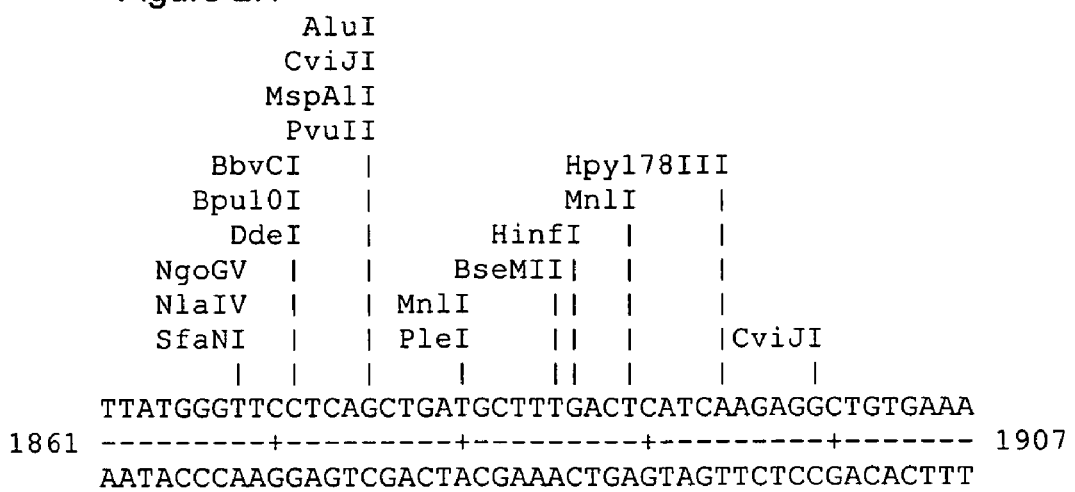

An open reading frame (ORF) encoding the chlamydial OMP (outer membrane protein) has been identified from the *C. pneumoniae* genome. The gene encoding this protein has been inserted into an expression plasmid and shown to confer immune protection against chlamydial infection. Accordingly, this OMP (outer membrane protein) and related polypeptides can be used to prevent and treat *Chlamydia* infection.

According to a first aspect of the invention, isolated polynucleotides are provided which encode *Chlamydia* polypeptides, whose amino acid sequences are shown in SEQ ID No: 2.

The term "isolated polynucleotide" is defined as a polynucleotide removed from the environment in which it naturally occurs. For example, a naturally-occurring DNA molecule present in the genome of a living bacteria or as part of a gene bank is not isolated, but the same molecule separated from the remaining part of the bacterial genome, as a result of, e.g., a cloning event (amplification), is isolated. Typically, an isolated DNA molecule is free from DNA regions (e.g., coding regions) with which it is immediately contiguous at the 5' or 3' end, in the naturally occurring genome. Such isolated polynucleotides may be part of a vector or a composition and still be defined as isolated in that such a vector or composition is not part of the natural environment of such polynucleotide.

The polynucleotide of the invention is either RNA or DNA (cDNA, genomic DNA, or synthetic DNA), or modifications, variants, homologs or fragments thereof. The DNA is either double-stranded or single-stranded, and, if single-stranded, is either the coding strand or the non-coding (anti-sense) strand. Any one of the sequences that encode the polypeptides of the invention as shown in SEQ ID No: 1 is (a) a coding sequence, (b) a ribonucleotide sequence derived from transcription of (a), or (c) a coding sequence which uses the redundancy or degeneracy of the genetic code to encode the same polypeptides. By "polypeptide" or "protein" is meant any chain of amino acids, regardless of length or post-translational modification (e.g., glycosylation or phosphorylation). Both terms are used interchangeably in the present application.

Consistent with the first aspect of the invention, amino acid sequences are provided which are homologous to SEQ ID No: 2. As used herein, "homologous amino acid sequence" is any polypeptide which is encoded, in whole or in part, by a nucleic acid sequence which hybridizes at 25-35° C. below critical melting temperature (Tm), to any portion of the nucleic acid sequence of SEQ ID No: 1. A homologous amino acid sequence is one that differs from an amino acid sequence shown in SEQ ID No: 2 by one or more conservative amino acid substitutions. Such a sequence also encompass serotypic variants (defined below) as well as sequences containing deletions or insertions which retain inherent characteristics of the polypeptide such as immunogenicity. Preferably, such a sequence is at least 75%, more preferably 80%, and most preferably 90% identical to SEQ ID No: 2.

Homologous amino acid sequences include sequences that are identical or substantially identical to SEQ ID No: 2. By "amino acid sequence substantially identical" is meant a sequence that is at least 90%, preferably 95%, more preferably 97%, and most preferably 99% identical to an amino acid sequence of reference and that preferably differs from the sequence of reference by a majority of conservative amino acid substitutions.

Conservative amino acid substitutions are substitutions among amino acids of the same class. These classes include, for example, amino acids having uncharged polar side chains, such as asparagine, glutamine, serine, threonine, and tyrosine; amino acids having basic side chains, such as lysine, arginine, and histidine; amino acids having acidic side chains, such as aspartic acid and glutamic acid; and amino acids having nonpolar side chains, such as glycine, alanine, valine, leucine, isoleucine, proline, phenylalanine, methionine, tryptophan, and cysteine.

Homology is measured using sequence analysis software such as Sequence Analysis Software Package of the Genetics Computer Group, University of Wisconsin Biotechnology Center, 1710 University Avenue, Madison, Wis. 53705. Amino acid sequences are aligned to maximize identity. Gaps may be artificially introduced into the sequence to attain proper alignment. Once the optimal alignment has been set up, the degree of homology is established by recording all of the positions in which the amino acids of both sequences are identical, relative to the total number of positions.

Homologous polynucleotide sequences are defined in a similar way. Preferably, a homologous sequence is one that is at least 45%, more preferably 60%, and most preferably 85% identical to the coding sequence of SEQ ID No: 1.

Consistent with the first aspect of the invention, polypeptides having a sequence homologous to SEQ ID No: 2 include naturally-occurring allelic variants, as well as mutants or any other non-naturally occurring variants that retain the inherent characteristics of the polypeptide of SEQ ID No: 2.

As is known in the art, an allelic variant is an alternate form of a polypeptide that is characterized as having a substitution, deletion, or addition of one or more amino acids that does not alter the biological function of the polypeptide. By "biological function" is meant the function of the polypeptide in the cells in which it naturally occurs, even if the function is not necessary for the growth or survival of the cells. For example, the biological function of a porin is to allow the entry into cells of compounds present in the extracellular medium. Biological function is distinct from antigenic property. A polypeptide can have more than one biological function.

Allelic variants are very common in nature. For example, a bacterial species such as *C. pneumoniae*, is usually represented by a variety of strains that differ from each other by minor allelic variations. Indeed, a polypeptide that fulfills the same biological function in different strains can have an amino acid sequence (and polynucleotide sequence) that is not identical in each of the strains. Despite this variation, an immune response directed generally against many allelic variants has been demonstrated. In studies of the Chlamydial MOMP antigen, cross-strain antibody binding plus neutralization of infectivity occurs despite amino acid sequence variation of MOMP from strain to strain, indicating that the MOMP, when used as an immunogen, is tolerant of amino acid variations.

Polynucleotides encoding homologous polypeptides or allelic variants are retrieved by polymerase chain reaction (PCR) amplification of genomic bacterial DNA extracted by conventional methods. This involves the use of synthetic oligonucleotide primers matching upstream and downstream of the 5' and 3' ends of the encoding domain. Suitable primers are designed according to the nucleotide sequence information provided in SEQ ID No:1. The procedure is as follows: a primer is selected which consists of 10 to 40, preferably 15 to 25 nucleotides. It is advantageous to select primers containing C and G nucleotides in a proportion sufficient to ensure efficient hybridization; i.e., an amount of C and G nucleotides of at least 40%, preferably 50% of the total nucleotide content. A standard PCR reaction contains typically 0.5 to 5 Units of Taq DNA polymerase per 100 µL, 20 to 200 µM deoxynucleotide each, preferably at equivalent concentrations, 0.5 to 2.5 mM magnesium over the total deoxynucleotide concentration, $10^5$ to $10^6$ target molecules, and about 20 pmol of each primer. About 25 to 50 PCR cycles are performed, with an annealing temperature 15° C. to 5° C. below the true Tm of the primers. A more stringent annealing temperature improves discrimination against incorrectly annealed primers and reduces incorporation of incorrect nucleotides at the 3' end of primers. A denaturation temperature of 95° C. to 97° C. is typical, although higher temperatures may be appropriate for dematuration of G+C-rich targets. The number of cycles performed depends on the starting concentration of target molecules, though typically more than 40 cycles is not recommended as non-specific background products tend to accumulate.

An alternative method for retrieving polynucleotides encoding homologous polypeptides or allelic variants is by hybridization screening of a DNA or RNA library. Hybridization procedures are well-known in the art and are described in Ausubel et al., (Ausubel et al., Current Protocols in Molecular Biology, John Wiley & Sons Inc., 1994), Silhavy et al. (Silhavy et al. Experiments with Gene Fusions, Cold Spring Harbor Laboratory Press, 1984), and Davis et al. (Davis et al. A Manual for Genetic Engineering: Advanced Bacterial Genetics, Cold Spring Harbor Laboratory Press, 1980)). Important parameters for optimizing hybridization conditions are reflected in a formula used to obtain the critical melting temperature above which two complementary DNA strands separate from each other (Casey & Davidson, Nucl. Acid Res. (1977) 4:1539). For polynucleotides of about 600 nucleotides or larger, this formula is as follows: Tm=81.5+ 0.41×(% G+C)+16.6 log (cation ion concentration)−0.63×(% formamide)−600/base number. Under appropriate stringency conditions, hybridization temperature (Th) is approximately 20 to 40° C., 20 to 25° C., or, preferably 30 to 40° C. below the calculated Tm. Those skilled in the art will understand that optimal temperature and salt conditions can be readily determined.

For the polynucleotides of the invention, stringent conditions are achieved for both pre-hybridizing and hybridizing incubations (i) within 4-16 hours at 42° C., in 6×SSC containing 50% formamide, or (ii) within 4-16 hours at 65° C. in an aqueous 6×SSC solution (1 M NaCl, 0.1 M sodium citrate (pH 7.0)). Typically, hybridization experiments are performed at a temperature from 60 to 68° C., e.g. 65° C. At such a temperature, stringent hybridization conditions can be achieved in 6×SSC, preferably in 2×SSC or 1×SSC, more preferably in 0.5×SSc, 0.3×SSC or 0.1×SSC (in the absence of formamide). 1×SSC contains 0.15 M NaCl and 0.015 M sodium citrate.

Useful homologs and fragments thereof that do not occur naturally are designed using known methods for identifying regions of an antigen that are likely to tolerate amino acid sequence changes and/or deletions. As an example, homologous polypeptides from different species are compared; conserved sequences are identified. The more divergent sequences are the most likely to tolerate sequence changes. Homology among sequences may be analyzed using, as an example, the BLAST homology searching algorithm of Altschul et al., Nucleic Acids Res.; 25:3389-3402 (1997). Alternatively, sequences are modified such that they become more reactive to T- and/or B-cells, based on computer-assisted analysis of probable T- or B-cell epitopes Yet another alternative is to mutate a particular amino acid residue or sequence within the polypeptide in vitro, then screen the mutant polypeptides for their ability to prevent or treat *Chlamydia* infection according to the method outlined below.

A person skilled in the art will readily understand that by following the screening process of this invention, it will be determined without undue experimentation whether a particular homolog of SEQ ID No. 2 may be useful in the prevention or treatment of *Chlamydia* infection. The screening procedure comprises the steps: immunizing an animal, preferably mouse, with the test homolog or fragment; inoculating the immunized animal with *Chlamydia*; and selecting those homologs or fragments which confer protection against *Chlamydia*.

By "conferring protection" is meant that there is a reduction in severity of any of the effects of *Chlamydia* infection, in comparison with a control animal which was not immunized with the test homolog or fragment.

Consistent with the first aspect of the invention, polypeptide derivatives are provided that are partial sequences of SEQ ID No. 2, partial sequences of polypeptide sequences homologous to SEQ ID No. 2, polypeptides derived from full-length polypeptides by internal deletion, and fusion proteins.

It is an accepted practice in the field of immunology to use fragments and variants of protein immunogens as vaccines, as all that is required to induce an immune response to a protein is a small (e.g., 8 to 10 amino acid) immunogenic region of the protein. Various short synthetic peptides corresponding to surface-exposed antigens of pathogens other than *Chlamydia* have been shown to be effective vaccine antigens against their respective pathogens, e.g. an 11 residue peptide of murine mammary tumor virus (Casey & Davidson, Nucl. Acid Res. (1977) 4:1539), a 16-residue peptide of Semliki Forest virus (Snijders et al., 1991. J. Gen. Virol. 72:557-565), and two overlapping peptides of 15 residues each from canine parvovirus (Langeveld et al., Vaccine 12(15):1473-1480, 1994).

Accordingly, it will be readily apparent to one skilled in the art, having read the present description, that partial sequences of SEQ ID No: 2 or their homologous amino acid sequences are inherent to the full-length sequences and are taught by the present invention. Such polypeptide fragments preferably are at least 12 amino acids in length. Advantageously, they are at least 20 amino acids, preferably at least 50 amino acids, more preferably at least 75 amino acids, and most preferably at least 100 amino acids in length.

Polynucleotides of 30 to 600 nucleotides encoding partial sequences of sequences homologous to SEQ ID No: 2 are retrieved by PCR amplification using the parameters outlined above and using primers matching the sequences upstream and downstream of the 5' and 3' ends of the fragment to be amplified. The template polynucleotide for such amplification is either the full length polynucleotide homologous to SEQ ID No: 1, or a polynucleotide contained in a mixture of polynucleotides such as a DNA or RNA library. As an alternative method for retrieving the partial sequences, screening hybridization is carried out under conditions described above and using the formula for calculating Tm. Where fragments of 30 to 600 nucleotides are to be retrieved, the calculated Tm is corrected by subtracting (600/polynucleotide size in base pairs) and the stringency conditions are defined by a hybridization temperature that is 5 to 10° C. below Tm. Where oligonucleotides shorter than 20-30 bases are to be obtained, the formula for calculating the Tm is as follows: $T_m=4\times(G+C)+2(A+T)$. For example, an 18 nucleotide fragment of 50% G+C would have an approximate Tm of 54° C. Short peptides that are fragments of SEQ ID No: 2 or its homologous sequences, are obtained directly by chemical synthesis (E. Gross and H. J. Meinhofer, 4 The Peptides: Analysis, Synthesis, Biology; Modern Techniques of Peptide Synthesis, John Wiley & Sons (1981), and M. Bodanzki, Principles of Peptide Synthesis, Springer-Verlag (1984)).

Useful polypeptide derivatives, e.g., polypeptide fragments, are designed using computer-assisted analysis of amino acid sequences. This would identify probable surface-exposed, antigenic regions (Hughes et al., 1992. Infect. Immun. 60(9):3497). Analysis of 6 amino acid sequences contained in SEQ ID No: 2, based on the product of flexibility and hydrophobicity propensities using the program SEQSEE (Wishart D S, et al. "SEQSEE: a comprehensive program suite for protein sequence analysis." *Comput Appl Biosci.* 1994 April;10(2):121-32), can reveal potential B- and T-cell epitopes which may be used as a basis for selecting useful immunogenic fragments and variants. This analysis uses a reasonable combination of external surface features that is likely to be recognized by antibodies. Probable T-cell epitopes for HLA-A0201 MHC subclass may be revealed by an algorithms that emulate an approach developed at the NIH (Parker K C, et al. "Peptide binding to MHC class I molecules: implications for antigenic peptide prediction." *Immunol Res* 1995;14(1):34-57).

Epitopes which induce a protective T cell-dependent immune response are present throughout the length of the polypeptide. However, some epitopes may be masked by secondary and tertiary structures of the polypeptide. To reveal such masked epitopes large internal deletions are created which remove much of the original protein structure and exposes the masked epitopes. Such internal deletions sometimes effect the additional advantage of removing immunodominant regions of high variability among strains.

Polynucleotides encoding polypeptide fragments and polypeptides having large internal deletions are constructed using standard methods (Ausubel et al., Current Protocols in Molecular Biology, John Wiley & Sons Inc., 1994). Such methods include standard PCR, inverse PCR, restriction enzyme treatment of cloned DNA molecules, or the method of Kunkel et al. (Kunkel et al. Proc. Natl. Acad. Sci. USA (1985) 82:448). Components for these methods and instructions for their use are readily available from various commercial sources such as Stratagene. Once the deletion mutants have been constructed, they are tested for their ability to prevent or treat *Chlamydia* infection as described above.

As used herein, a fusion polypeptide is one that contains a polypeptide or a polypeptide derivative of the invention fused at the N- or C-terminal end to any other polypeptide (hereinafter referred to as a peptide tail). A simple way to obtain such a fusion polypeptide is by translation of an in-frame fusion of the polynucleotide sequences, i.e., a hybrid gene. The hybrid gene encoding the fusion polypeptide is inserted into an expression vector which is used to transform or transfect a host cell. Alternatively, the polynucleotide sequence encoding the polypeptide or polypeptide derivative is inserted into an expression vector in which the polynucleotide encoding the peptide tail is already present. Such vectors and instructions for their use are commercially available, e.g. the pMal-c2 or pMal-p2 system from New England Biolabs, in which the peptide tail is a maltose binding protein, the glutathione-S-transferase system of Pharmacia, or the His-Tag system available from Novagen. These and other expression systems provide convenient means for further purification of polypeptides and derivatives of the invention.

An advantageous example of a fusion polypeptide is one where the polypeptide or homolog or fragment of the invention is fused to a polypeptide having adjuvant activity, such as subunit B of either cholera toxin or *E. coli* heat-labile toxin. Another advantageous fusion is one where the polypeptide, homolog or fragment is fused to a strong T-cell epitope or B-cell epitope. Such an epitope may be one known in the art (e.g. the Hepatitis B virus core antigen, D. R. Millich et al., "Antibody production to the nucleocapsid and envelope of the Hepatitis B virus primed by a single synthetic T cell site", Nature. 1987. 329:547-549), or one which has been identified in another polypeptide of the invention based on computer-assisted analysis of probable T- or B-cell epitopes. Consistent with this aspect of the invention is a fusion polypeptide comprising T- or B-cell epitopes from SEQ ID No: 2 or its homolog or fragment, wherein the epitopes are derived from multiple variants of said polypeptide or homolog or fragment, each variant differing from another in the location and sequence of its epitope within the polypeptide. Such a fusion is effective in the prevention and treatment of *Chlamydia* infection since it optimizes the T- and B-cell response to the overall polypeptide, homolog or fragment.

To effect fusion, the polypeptide of the invention is fused to the N-, or preferably, to the C-terminal end of the polypeptide having adjuvant activity or T- or B-cell epitope. Alternatively, a polypeptide fragment of the invention is inserted internally within the amino acid sequence of the polypeptide having adjuvant activity. The T- or B-cell epitope may also be inserted internally within the amino acid sequence of the polypeptide of the invention.

Consistent with the first aspect, the polynucleotides of the invention also encode hybrid precursor polypeptides containing heterologous signal peptides, which mature into polypeptides of the invention. By "heterologous signal peptide" is meant a signal peptide that is not found in naturally-occurring precursors of polypeptides of the invention.

Polynucleotide molecules according to the invention, including RNA, DNA, or modifications or combinations thereof, have various applications. A DNA molecule is used, for example, (i) in a process for producing the encoded polypeptide in a recombinant host system, (ii) in the construction of vaccine vectors such as poxviruses, which are further used in methods and compositions for preventing and/or treating *Chlamydia* infection, (iii) as a vaccine agent (as well as an RNA molecule), in a naked form or formulated with a delivery vehicle and, (iv) in the construction of attenuated *Chlamydia* strains that can over-express a polynucleotide of the invention or express it in a non-toxic, mutated form.

Accordingly, a second aspect of the invention encompasses (i) an expression cassette containing a DNA molecule of the invention placed under the control of the elements required for expression, in particular under the control of an appropriate promoter; (ii) an expression vector containing an expression cassette of the invention; (iii) a procaryotic or eucaryotic cell transformed or transfected with an expression cassette and/or vector of the invention, as well as (iv) a process for producing a polypeptide or polypeptide derivative encoded by a polynucleotide of the invention, which involves culturing a procaryotic or eucaryotic cell transformed or transfected with an expression cassette and/or vector of the invention, under conditions that allow expression of the DNA molecule of the invention and, recovering the encoded polypeptide or polypeptide derivative from the cell culture.

A recombinant expression system is selected from procaryotic and eucaryotic hosts. Eucaryotic hosts include yeast cells (e.g., *Saccharomyces cerevisiae* or *Pichia pastoris*), mammalian cells (e.g., COS1, NIH3T3, or JEG3 cells), arthropods cells (e.g., *Spodoptera frugiperda* (SF9) cells), and plant cells. A preferred expression system is a procaryotic host such as *E. coli*. Bacterial and eucaryotic cells are available from a number of different sources including commercial sources to those skilled in the art, e.g., the American Type Culture Collection (ATCC; 10801 University Boulevard, Manassas, Va. 20110-2209). Commercial sources of cells used for recombinant protein expression also provide instructions for usage of the cells.

The choice of the expression system depends on the features desired for the expressed polypeptide. For example, it may be useful to produce a polypeptide of the invention in a particular lipidated form or any other form.

One skilled in the art would redily understand that not all vectors and expression control sequences and hosts would be expected to express equally well the polynucleotides of this invention. With the guidelines described below, however, a selection of vectors, expression control sequences and hosts may be made without undue experimentation and without departing from the scope of this invention.

In selecting a vector, the host must be chosen that is compatible with the vector which is to exist and possibly replicate in it. Considerations are made with respect to the vector copy number, the ability to control the copy number, expression of other proteins such as antibiotic resistance. In selecting an expression control sequence, a number of variables are considered. Among the important variable are the relative strength of the sequence (e.g. the ability to drive expression under various conditions), the ability to control the sequence's function, compatibility between the polynucleotide to be expressed and the control sequence (e.g. secondary structures are considered to avoid hairpin structures which prevent efficient transcription). In selecting the host, unicellular hosts are selected which are compatible with the selected vector, tolerant of any possible toxic effects of the expressed product, able to secrete the expressed product efficiently if such is desired, to be able to express the product in the desired conformation, to be easily scaled up, and to which ease of purification of the final product.

The choice of the expression cassette depends on the host system selected as well as the features desired for the expressed polypeptide. Typically, an expression cassette includes a promoter that is functional in the selected host system and can be constitutive or inducible; a ribosome binding site; a start codon (ATG) if necessary; a region encoding a signal peptide, e.g., a lipidation signal peptide; a DNA molecule of the invention; a stop codon; and optionally a 3' terminal region (translation and/or transcription terminator). The signal peptide encoding region is adjacent to the polynucleotide of the invention and placed in proper reading frame. The signal peptide-encoding region is homologous or heterologous to the DNA molecule encoding the mature polypeptide and is compatible with the secretion apparatus of the host used for expression. The open reading frame constituted by the DNA molecule of the invention, solely or together with the signal peptide, is placed under the control of the promoter so that transcription and translation occur in the host system. Promoters and signal peptide encoding regions are widely known and available to those skilled in the art and include, for example, the promoter of *Salmonella typhimurium* (and derivatives) that is inducible by arabinose (promoter araB) and is functional in Gram-negative bacteria such as *E. coli* (as described in U.S. Pat. No. 5,028,530 and in Cagnon et al., (Cagnon et al., Protein Engineering (1991) 4(7):843)); the promoter of the gene of bacteriophage T7 encoding RNA polymerase, that is functional in a number of *E. coli* strains expressing T7 polymerase (described in U.S. Pat. No. 4,952,496); OspA lipidation signal peptide; and RlpB lipidation signal peptide (Takase et al., J. Bact. (1987) 169:5692).

The expression cassette is typically part of an expression vector, which is selected for its ability to replicate in the chosen expression system. Expression vectors (e.g., plasmids or viral vectors) can be chosen, for example, from those described in Pouwels et al. (Cloning Vectors: A Laboratory Manual 1985, Supp. 1987). Suitable expression vectors can be purchased from various commercial sources.

Methods for transforming/transfecting host cells with expression vectors are well-known in the art and depend on the host system selected as described in Ausubel et al., (Ausubel et al., Current Protocols in Molecular Biology, John Wiley & Sons Inc., 1994).

Upon expression, a recombinant polypeptide of the invention (or a polypeptide derivative) is produced and remains in the intracellular compartment, is secreted/excreted in the extracellular medium or in the periplasmic space, or is embedded in the cellular membrane. The polypeptide is recovered in a substantially purified form from the cell extract or from the supernatant after centrifugation of the recombinant cell culture. Typically, the recombinant polypeptide is purified by antibody-based affinity purification or by other well-known methods that can be readily adapted by a person skilled in the art, such as fusion of the polynucleotide encoding the polypeptide or its derivative to a small affinity binding domain. Antibodies useful for purifying by immunoaffinity the polypeptides of the invention are obtained as described below.

A polynucleotide of the invention can also be useful as a vaccine. There are two major routes, either using a viral or bacterial host as gene delivery vehicle (live vaccine vector) or administering the gene in a free form, e.g., inserted into a plasmid. Therapeutic or prophylactic efficacy of a polynucleotide of the invention is evaluated as described below.

Accordingly, a third aspect of the invention provides (i) a vaccine vector such as a poxvirus, containing a DNA molecule of the invention, placed under the control of elements required for expression; (ii) a composition of matter comprising a vaccine vector of the invention, together with a diluent or carrier; specifically (iii) a pharmaceutical composition containing a therapeutically or prophylactically effective amount of a vaccine vector of the invention; (iv) a method for inducing an immune response against *Chlamydia* in a mammal (e.g., a human; alternatively, the method can be used in veterinary applications for treating or preventing *Chlamydia* infection of animals, e.g., cats or birds), which involves administering to the mammal an immunogenically effective amount of a vaccine vector of the invention to elicit a protective or therapeutic immune response to *Chlamydia*; and particularly, (v) a method for preventing and/or treating a *Chlamydia* (e.g., *C. trachomatis, C. psittaci, C. pneumonia, C. pecorum*) infection, which involves administering a prophylactic or therapeutic amount of a vaccine vector of the invention to an infected individual. Additionally, the third aspect of the invention encompasses the use of a vaccine vector of the invention in the preparation of a medicament for preventing and/or treating *Chlamydia* infection.

As used herein, a vaccine vector expresses one or several polypeptides or derivatives of the invention. The vaccine vector may express additionally a cytokine, such as interleukin-2 (IL-2) or interleukin-12 (IL-12), that enhances the immune response (adjuvant effect). It is understood that each of the components to be expressed is placed under the control of elements required for expression in a mammalian cell.

Consistent with the third aspect of the invention is a composition comprising several vaccine vectors, each of them capable of expressing a polypeptide or derivative of the invention. A composition may also comprise a vaccine vector capable of expressing an additional *Chlamydia* antigen, or a subunit, fragment, homolog, mutant, or derivative thereof; optionally together with or a cytokine such as IL-2 or IL-12.

Vaccination methods for treating or preventing infection in a mammal comprises use of a vaccine vector of the invention to be administered by any conventional route, particularly to a mucosal (e.g., ocular, intranasal, oral, gastric, pulmonary, intestinal, rectal, vaginal, or urinary tract) surface or via the parenteral (e.g., subcutaneous, intradermal, intramuscular, intravenous, or intraperitoneal) route. Preferred routes depend upon the choice of the vaccine vector. Treatment may be effected in a single dose or repeated at intervals. The appropriate dosage depends on various parameters understood by skilled artisans such as the vaccine vector itself, the route of administration or the condition of the mammal to be vaccinated (weight, age and the like).

Live vaccine vectors available in the art include viral vectors such as adenoviruses and poxviruses as well as bacterial vectors, e.g., *Shigella, Salmonella, Vibrio cholerae, Lactobacillus*, Bacille bilié de Calmette-Guérin (BCG), and *Streptococcus*.

An example of an adenovirus vector, as well as a method for constructing an adenovirus vector capable of expressing a DNA molecule of the invention, are described in U.S. Pat. No. 4,920,209. Poxvirus vectors include vaccinia and canary pox virus, described in U.S. Pat. No. 4,722,848 and U.S. Pat. No. 5,364,773, respectively. (Also see, e.g., Tartaglia et al., Virology (1992) 188:217) for a description of a vaccinia virus vector and Taylor et al, Vaccine (1995) 13:539 for a reference of a canary pox.) Poxvirus vectors capable of expressing a polynucleotide of the invention are obtained by homologous recombination as described in Kieny et al., Nature (1984) 312:163 so that the polynucleotide of the invention is inserted in the viral genome under appropriate conditions for expression in mammalian cells. Generally, the dose of vaccine viral vector, for therapeutic or prophylactic use, can be of from about $1 \times 10^4$ to about $1 \times 10^{11}$, advantageously from about $1 \times 10^7$ to about $1 \times 10^{10}$, preferably of from about $1 \times 10^7$ to about $1 \times 10^9$ plaque-forming units per kilogram. Preferably, viral vectors are administered parenterally; for example, in 3 doses, 4 weeks apart. It is preferable to avoid adding a chemical adjuvant to a composition containing a viral vector of the invention and thereby minimizing the immune response to the viral vector itself.

Non-toxicogenic *Vibrio cholerae* mutant strains that are useful as a live oral vaccine are known. Mekalanos et al., Nature (1983) 306:551 and U.S. Pat. No. 4,882,278 describe strains which have a substantial amount of the coding sequence of each of the two ctxA alleles deleted so that no functional *cholerae* toxin is produced. WO 92/11354 describes a strain in which the irgA locus is inactivated by mutation; this mutation can be combined in a single strain with ctxA mutations. WO 94/01533 describes a deletion mutant lacking functional ctxA and attRS1 DNA sequences. These mutant strains are genetically engineered to express heterologous antigens, as described in WO 94/19482. An effective vaccine dose of a *Vibrio cholerae* strain capable of expressing a polypeptide or polypeptide derivative encoded by a DNA molecule of the invention contains about $1 \times 10^5$ to about $1 \times 10^9$, preferably about $1 \times 10^6$ to about $1 \times 10^8$, viable bacteria in a volume appropriate for the selected route of administration. Preferred routes of administration include all mucosal routes; most preferably, these vectors are administered intranasally or orally.

Attenuated *Salmonella typhimurium* strains, genetically engineered for recombinant expression of heterologous antigens or not, and their use as oral vaccines are described in Nakayama et al. (Bio/Technology (1988) 6:693) and WO 92/11361. Preferred routes of administration include all mucosal routes; most preferably, these vectors are administered intranasally or orally.

Other bacterial strains used as vaccine vectors in the context of the present invention are described for *Shigella flexneri* in High et al., EMBO (1992) 11:1991 and Sizemore et al., Science (1995) 270:299; for *Streptococcus gordonii* in Medaglini et al., Proc. Natl. Acad. Sci. USA (1995) 92:6868; and for Bacille Calmette Guerin in Flynn J. L., Cell. Mol. Biol. (1994) 40 (suppl. I):31, WO 88/06626, WO 90/00594, WO 91/13157, WO 92/01796, and WO 92/21376.

In bacterial vectors, the polynucleotide of the invention is inserted into the bacterial genome or remains in a free state as part of a plasmid.

The composition comprising a vaccine bacterial vector of the present invention may further contain an adjuvant. A number of adjuvants are known to those skilled in the art. Preferred adjuvants are selected as provided below.

Accordingly, a fourth aspect of the invention provides (i) a composition of matter comprising a polynucleotide of the invention, together with a diluent or carrier; (ii) a pharmaceutical composition comprising a therapeutically or prophylactically effective amount of a polynucleotide of the invention; (iii) a method for inducing an immune response against *Chlamydia* in a mammal by administration of an immunogenically effective amount of a polynucleotide of the invention to elicit a protective immune response to *Chlamydia*; and particularly, (iv) a method for preventing and/or treating *Chlamydia* (e.g., *C. trachomatis, C. psittaci, C. pneumoniae*, or *C. pecorum*) infection, by administering a prophylactic or therapeutic amount of a polynucleotide of the invention to an infected individual. Additionally, the fourth aspect of the invention encompasses the use of a polynucleotide of the invention in the preparation of a medicament for preventing and/or treating *Chlamydia* infection. A preferred use includes the use of a DNA molecule placed under conditions for expression in a mammalian cell, especially in a plasmid that is unable to replicate in mammalian cells and to substantially integrate in a mammalian genome.

Use of the polynucleotides of the invention include their administration to a mammal as a vaccine, for therapeutic or prophylactic purposes. Such polynucleotides are used in the form of DNA as part of a plasmid that is unable to replicate in a mammalian cell and unable to integrate into the mammalian genome. Typically, such a DNA molecule is placed under the control of a promoter suitable for expression in a mammalian cell. The promoter functions either ubiquitously or tissue-specifically. Examples of non-tissue specific promoters include the early Cytomegalovirus (CMV) promoter (described in U.S. Pat. No. 4,168,062) and the Rous Sarcoma Virus promoter (described in Norton & Coffin, Molec. Cell Biol. (1985) 5:281). An example of a tissue-specific promoter is the desmin promoter which drives expression in muscle cells (Li et al., Gene (1989) 78:243, Li & Paulin, J. Biol. Chem. (1991) 266:6562 and Li & Paulin, J. Biol. Chem. (1993) 268:10403). Use of promoters is well-known to those skilled in the art. Useful vectors are described in numerous publications, specifically WO 94/21797 and Hartikka et al., Human Gene Therapy (1996) 7:1205.

Polynucleotides of the invention which are used as vaccines encode either a precursor or a mature form of the corresponding polypeptide. In the precursor form, the signal peptide is either homologous or heterologous. In the latter case, a eucaryotic leader sequence such as the leader sequence of the tissue-type plasminogen factor (tPA) is preferred.

As used herein, a composition of the invention contains one or several polynucleotides with optionally at least one additional polynucleotide encoding another *Chlamydia* antigen such as urease subunit A, B, or both, or a fragment, derivative, mutant, or analog thereof. The composition may also contain an additional polynucleotide encoding a cytokine, such as interleukin-2 (IL-2) or interleukin-12 (IL-12) so that the immune response is enhanced. These additional polynucleotides are placed under appropriate control for expression. Advantageously, DNA molecules of the invention and/or additional DNA molecules to be included in the same composition, are present in the same plasmid.

Standard techniques of molecular biology for preparing and purifying polynucleotides are used in the preparation of polynucleotide therapeutics of the invention. For use as a vaccine, a polynucleotide of the invention is formulated according to various methods outlined below.

One method utilizes the polynucleotide in a naked form, free of any delivery vehicles. Such a polynucleotide is simply diluted in a physiologically acceptable solution such as sterile saline or sterile buffered saline, with or without a carrier. When present, the carrier preferably is isotonic, hypotonic, or weakly hypertonic, and has a relatively low ionic strength, such as provided by a sucrose solution, e.g., a solution containing 20% sucrose.

An alternative method utilizes the polynucleotide in association with agents that assist in cellular uptake. Examples of such agents are (i) chemicals that modify cellular permeability, such as bupivacaine (see, e.g., WO 94/16737), (ii) liposomes for encapsulation of the polynucleotide, or (iii) cationic lipids or silica, gold, or tungsten microparticles which associate themselves with the polynucleotides.

Anionic and neutral liposomes are well-known in the art (see, e.g., Liposomes: A Practical Approach, RPC New Ed, IRL press (1990), for a detailed description of methods for making liposomes) and are useful for delivering a large range of products, including polynucleotides.

Cationic lipids are also known in the art and are commonly used for gene delivery. Such lipids include Lipofectin™ also known as DOTMA (N-[1-(2,3-dioleyloxy)propyl]-N,N,N-trimethylammonium chloride), DOTAP (1,2-bis(oleyloxy)-3-(trimethylammonio)propane), DDAB (dimethyldioctadecylammonium bromide), DOGS (dioctadecylamidologlycyl spermine) and cholesterol derivatives such as DC-Chol (3 beta-(N-(N',N'-dimethyl aminomethane)-carbamoyl)cholesterol). A description of these cationic lipids can be found in EP 187,702, WO 90/11092, U.S. Pat. No. 5,283,185, WO 91/15501, WO 95/26356, and U.S. Pat. No. 5,527,928. Cationic lipids for gene delivery are preferably used in association with a neutral lipid such as DOPE (dioleyl phosphatidylethanolamine), as described in WO 90/11092 as an example.

Formulation containing cationic liposomes may optionally contain other transfection-facilitating compounds. A number of them are described in WO 93/18759, WO 93/19768, WO 94/25608, and WO 95/02397. They include spermine derivatives useful for facilitating the transport of DNA through the nuclear membrane (see, for example, WO 93/18759) and membrane-permeabilizing compounds such as GALA, Gramicidine S, and cationic bile salts (see, for example, WO 93/19768).

Gold or tungsten microparticles are used for gene delivery, as described in WO 91/00359, WO 93/17706, and Tang et al. Nature (1992) 356:152. The microparticle-coated polynucleotide is injected via intradermal or intraepidermal routes using a needleless injection device ("gene gun"), such as those described in U.S. Pat. No. 4,945,050, U.S. Pat. No. 5,015,580, and WO 94/24263.

The amount of DNA to be used in a vaccine recipient depends, e.g., on the strength of the promoter used in the DNA construct, the immunogenicity of the expressed gene product, the condition of the mammal intended for administration (e.g., the weight, age, and general health of the mammal), the mode of administration, and the type of formulation. In general, a therapeutically or prophylactically effective dose from about 1 µg to about 1 mg, preferably, from about 10 µg to about 800 µg and, more preferably, from about 25 µg to about 250 µg, can be administered to human adults. The administration can be achieved in a single dose or repeated at intervals.

The route of administration is any conventional route used in the vaccine field. As general guidance, a polynucleotide of the invention is administered via a mucosal surface, e.g., an ocular, intranasal, pulmonary, oral, intestinal, rectal, vaginal, and urinary tract surface; or via a parenteral route, e.g., by an intravenous, subcutaneous, intraperitoneal, intradermal, intraepidermal, or intramuscular route. The choice of administration route depends on the formulation that is selected. A polynucleotide formulated in association with bupivacaine is advantageously administered into muscles. When a neutral or anionic liposome or a cationic lipid, such as DOTMA or DC-Chol, is used, the formulation can be advantageously injected via intravenous, intranasal (aerosolization), intramuscular, intradermal, and subcutaneous routes. A polynucleotide in a naked form can advantageously be administered via the intramuscular, intradermal, or sub-cutaneous routes.

Although not absolutely required, such a composition can also contain an adjuvant. If so, a systemic adjuvant that does not require concomitant administration in order to exhibit an adjuvant effect is preferable such as, e.g., QS21, which is described in U.S. Pat. No. 5,057,546.

The sequence information provided in the present application enables the design of specific nucleotide probes and primers that are used for diagnostic purposes. Accordingly, a fifth aspect of the invention provides a nucleotide probe or primer having a sequence found in or derived by degeneracy of the genetic code from a sequence shown in SEQ ID No:1.

The term "probe" as used in the present application refers to DNA (preferably single stranded) or RNA molecules (or modifications or combinations thereof) that hybridize under the stringent conditions, as defined above, to nucleic acid molecules having SEQ ID No:1 or to sequences homologous to SEQ ID No:1, or to its complementary or anti-sense sequence. Generally, probes are significantly shorter than full-length sequences. Such probes contain from about 5 to about 100, preferably from about 10 to about 80, nucleotides. In particular, probes have sequences that are at least 75%, preferably at least 85%, more preferably 95% homologous to a portion of SEQ ID No:1 or that are complementary to such sequences. Probes may contain modified bases such as inosine, methyl-5-deoxycytidine, deoxyuridine, dimethylamino-5-deoxyuridine, or diamino-2,6-purine. Sugar or phosphate residues may also be modified or substituted. For example, a deoxyribose residue may be replaced by a polyamide (Nielsen et al., Science (1991) 254:1497) and phosphate residues may be replaced by ester groups such as diphosphate, alkyl, arylphosphonate and phosphorothioate esters. In addition, the 2'-hydroxyl group on ribonucleotides may be modified by including such groups as alkyl groups.

Probes of the invention are used in diagnostic tests, as capture or detection probes. Such capture probes are conventionally immobilized on a solid support, directly or indirectly, by covalent means or by passive adsorption. A detection probe is labelled by a detection marker selected from: radioactive isotopes, enzymes such as peroxidase, alkaline phosphatase, and enzymes able to hydrolyze a chromogenic, fluorogenic, or luminescent substrate, compounds that are chromogenic, fluorogenic, or luminescent, nucleotide base analogs, and biotin.

Probes of the invention are used in any conventional hybridization technique, such as dot blot (Maniatis et al., Molecular Cloning: A Laboratory Manual (1982) Cold Spring Harbor Laboratory Press, Cold Spring Harbor, N.Y.), Southern blot (Southern, J. Mol. Biol. (1975) 98:503), northern blot (identical to Southern blot with the exception that RNA is used as a target), or the sandwich technique (Dunn et al., Cell (1977) 12:23). The latter technique involves the use of a specific capture probe and/or a specific detection probe with nucleotide sequences that at least partially differ from each other.

A primer is a probe of usually about 10 to about 40 nucleotides that is used to initiate enzymatic polymerization of DNA in an amplification process (e.g., PCR), in an elongation process, or in a reverse transcription method. Primers used in diagnostic methods involving PCR are labeled by methods known in the art.

As described herein, the invention also encompasses (i) a reagent comprising a probe of the invention for detecting and/or identifying the presence of *Chlamydia* in a biological material; (ii) a method for detecting and/or identifying the presence of *Chlamydia* in a biological material, in which (a) a sample is recovered or derived from the biological material, (b) DNA or RNA is extracted from the material and denatured, and (c) exposed to a probe of the invention, for example, a capture, detection probe or both, under stringent hybridization conditions, such that hybridization is detected; and (iii) a method for detecting and/or identifying the presence of *Chlamydia* in a biological material, in which (a) a sample is recovered or derived from the biological material, (b) DNA is extracted therefrom, (c) the extracted DNA is primed with at least one, and preferably two, primers of the invention and amplified by polymerase chain reaction, and (d) the amplified DNA fragment is produced.

It is apparent that disclosure of polynucleotide sequences of SEQ ID No:1, its homologs and partial sequences enable their corresponding amino acid sequences. Accordingly, a sixth aspect of the invention features a substantially purified polypeptide or polypeptide derivative having an amino acid sequence encoded by a polynucleotide of the invention.

A "substantially purified polypeptide" as used herein is defined as a polypeptide that is separated from the environment in which it naturally occurs and/or that is free of the majority of the polypeptides that are present in the environment in which it was synthesized. For example, a substantially purified polypeptide is free from cytoplasmic polypeptides. Those skilled in the art would readily understand that the polypeptides of the invention may be purified from a natural source, i.e., a *Chlamydia* strain, or produced by recombinant means.

Consistent with the sixth aspect of the invention are polypeptides, homologs or fragments which are modified or treated to enhance their immunogenicity in the target animal, in whom the polypeptide, homolog or fragments are intended to confer protection against *Chlamydia*. Such modifications or treatments include: amino acid substitutions with an amino acid derivative such as 3-methylhistidine, 4-hydroxyproline, 5-hydroxylysine etc., modifications or deletions which are carried out after preparation of the polypeptide, homolog or fragment, such as the modification of free amino, carboxyl or hydroxyl side groups of the amino acids.

Identification of homologous polypeptides or polypeptide derivatives encoded by polynucleotides of the invention which have specific antigenicity is achieved by screening for cross-reactivity with an antiserum raised against the polypeptide of reference having an amino acid sequence of SEQ ID No:1. The procedure is as follows: a monospecific hyperimmune antiserum is raised against a purified reference polypeptide, a fusion polypeptide (for example, an expression product of MBP, GST, or His-tag systems, the description and instructions for use of which are contained in Invitrogen product manuals for pcDNA3.1/Myc-His(+) A, B, and C and for the Xpress™ System Protein Purification), or a synthetic peptide predicted to be antigenic. Where an antiserum is raised against a fusion polypeptide, two different fusion systems are employed. Specific antigenicity can be determined according to a number of methods, including Western blot (Towbin et al., Proc. Natl. Acad. Sci. USA (1979) 76:4350), dot blot, and ELISA, as described below.

In a Western blot assay, the product to be screened, either as a purified preparation or a total *E. coli* extract, is submitted to SDS-Page electrophoresis as described by Laemmli (Nature (1970) 227:680). After transfer to a nitrocellulose membrane, the material is further incubated with the monospecific hyperimmune antiserum diluted in the range of dilutions from about 1:5 to about 1:5000, preferably from about 1:100 to about 1:500. Specific antigenicity is shown once a band corresponding to the product exhibits reactivity at any of the dilutions in the above range.

In an ELISA assay, the product to be screened is preferably used as the coating antigen. A purified preparation is preferred, although a whole cell extract can also be used. Briefly, about 100 μl of a preparation at about 10 μg protein/ml are distributed into wells of a 96-well polycarbonate ELISA plate. The plate is incubated for 2 hours at 37° C. then overnight at 4° C. The plate is washed with phosphate buffer saline (PBS) containing 0.05% Tween 20 (PBS/Tween buffer). The wells are saturated with 250 μl PBS containing 1% bovine serum albumin (BSA) to prevent non-specific antibody binding. After 1 hour incubation at 37° C., the plate is washed with PBS/Tween buffer. The antiserum is serially diluted in PBS/Tween buffer containing 0.5% BSA. 100 μl of dilutions are added per well. The plate is incubated for 90 minutes at 37° C., washed and evaluated according to standard procedures. For example, a goat anti-rabbit peroxidase conjugate is added to the wells when specific antibodies were raised in rabbits. Incubation is carried out for 90 minutes at 37° C. and the plate is washed. The reaction is developed with the appropriate substrate and the reaction is measured by colorimetry (absorbance measured spectrophotometrically).

Under the above experimental conditions, a positive reaction is shown by O.D. values greater than a non immune control serum.

In a dot blot assay, a purified product is preferred, although a whole cell extract can also be used. Briefly, a solution of the product at about 100 µg/ml is serially two-fold diluted in 50 mM Tris-HCl (pH 7.5). 100 µl of each dilution are applied to a nitrocellulose membrane 0.45 µm set in a 96-well dot blot apparatus (Biorad). The buffer is removed by applying vacuum to the system. Wells are washed by addition of 50 mM Tris-HCl (pH 7.5) and the membrane is air-dried. The membrane is saturated in blocking buffer (50 mM Tris-HCl (pH 7.5) 0.15 M NaCl, 10 g/L skim milk) and incubated with an antiserum dilution from about 1:50 to about 1:5000, preferably about 1:500. The reaction is revealed according to standard procedures. For example, a goat anti-rabbit peroxidase conjugate is added to the wells when rabbit antibodies are used. Incubation is carried out 90 minutes at 37° C. and the blot is washed. The reaction is developed with the appropriate substrate and stopped. The reaction is measured visually by the appearance of a colored spot, e.g., by colorimetry. Under the above experimental conditions, a positive reaction is shown once a colored spot is associated with a dilution of at least about 1:5, preferably of at least about 1:500.

Therapeutic or prophylactic efficacy of a polypeptide or derivative of the invention can be evaluated as described below. A seventh aspect of the invention provides (i) a composition of matter comprising a polypeptide of the invention together with a diluent or carrier; specifically (ii) a pharmaceutical composition containing a therapeutically or prophylactically effective amount of a polypeptide of the invention; (iii) a method for inducing an immune response against *Chlamydia* in a mammal, by administering to the mammal an immunogenically effective amount of a polypeptide of the invention to elicit a protective immune response to *Chlamydia*; and particularly, (iv) a method for preventing and/or treating a *Chlamydia* (e.g., *C. trachomatis. C. psittaci, C. pneumoniae.* or *C. pecorum*) infection, by administering a prophylactic or therapeutic amount of a polypeptide of the invention to an infected individual. Additionally, the seventh aspect of the invention encompasses the use of a polypeptide of the invention in the preparation of a medicament for preventing and/or treating *Chlamydia* infection.

As used herein, the immunogenic compositions of the invention are administered by conventional routes known the vaccine field, in particular to a mucosal (e.g., ocular, intranasal, pulmonary, oral, gastric, intestinal, rectal, vaginal, or urinary tract) surface or via the parenteral (e.g., subcutaneous, intradermal, intramuscular, intravenous, or intraperitoneal) route. The choice of administration route depends upon a number of parameters, such as the adjuvant associated with the polypeptide. If a mucosal adjuvant is used, the intranasal or oral route is preferred. If a lipid formulation or an aluminum compound is used, the parenteral route is preferred with the sub-cutaneous or intramuscular route being most preferred. The choice also depends upon the nature of the vaccine agent. For example, a polypeptide of the invention fused to CTB or LTB is best administered to a mucosal surface.

As used herein, the composition of the invention contains one or several polypeptides or derivatives of the invention. The composition optionally contains at least one additional *Chlamydia* antigen, or a subunit, fragment, homolog, mutant, or derivative thereof.

For use in a composition of the invention, a polypeptide or derivative thereof is formulated into or with liposomes, preferably neutral or anionic liposomes, microspheres, ISCOMS, or virus-like-particles (VLPs) to facilitate delivery and/or enhance the immune response. These compounds are readily available to one skilled in the art; for example, see Liposomes: A Practical Approach, RCP New Ed, IRL press (1990).

Adjuvants other than liposomes and the like are also used and are known in the art. Adjuvants may protect the antigen from rapid dispersal by sequestering it in a local deposit, or they may contain substances that stimulate the host to secrete factors that are chemotactic for macrophages and other components of the immune system. An appropriate selection can conventionally be made by those skilled in the art, for example, from those described below (under the eleventh aspect of the invention).

Treatment is achieved in a single dose or repeated as necessary at intervals, as can be determined readily by one skilled in the art. For example, a priming dose is followed by three booster doses at weekly or monthly intervals. An appropriate dose depends on various parameters including the recipient (e.g., adult or infant), the particular vaccine antigen, the route and frequency of administration, the presence/absence or type of adjuvant, and the desired effect (e.g., protection and/or treatment), as can be determined by one skilled in the art. In general, a vaccine antigen of the invention is administered by a mucosal route in an amount from about 10 µg to about 500 mg, preferably from about 1 mg to about 200 mg. For the parenteral route of administration, the dose usually does not exceed about 1 mg, preferably about 100 µg.

When used as vaccine agents, polynucleotides and polypeptides of the invention may be used sequentially as part of a multistep immunization process. For example, a mammal is initially primed with a vaccine vector of the invention such as a pox virus, e.g., via the parenteral route, and then boosted twice with the polypeptide encoded by the vaccine vector, e.g., via the mucosal route. In another example, liposomes associated with a polypeptide or derivative of the invention is also used for priming, with boosting being carried out mucosally using a soluble polypeptide or derivative of the invention in combination with a mucosal adjuvant (e.g., LT).

A polypeptide derivative of the invention is also used in accordance with the seventh aspect as a diagnostic reagent for detecting the presence of anti-*Chlamydia* antibodies, e.g., in a blood sample. Such polypeptides are about 5 to about 80, preferably about 10 to about 50 amino acids in length. They are either labeled or unlabeled, depending upon the diagnostic method. Diagnostic methods involving such a reagent are described below.

Upon expression of a DNA molecule of the invention, a polypeptide or polypeptide derivative is produced and purified using known laboratory techniques. As described above, the polypeptide or polypeptide derivative may be produced as a fusion protein containing a fused tail that facilitates purification. The fusion product is used to immunize a small mammal, e.g., a mouse or a rabbit, in order to raise antibodies against the polypeptide or polypeptide derivative (monospecific antibodies). Accordingly, an eighth aspect of the invention provides a monospecific antibody that binds to a polypeptide or polypeptide derivative of the invention.

By "monospecific antibody" is meant an antibody that is capable of reacting with a unique naturally-occurring *Chlamydia* polypeptide. An antibody of the invention is either polyclonal or monoclonal. Monospecific antibodies may be recombinant, e.g., chimeric (e.g., constituted by a variable region of murine origin associated with a human constant region), humanized (a human immunoglobulin constant backbone together with hypervariable region of animal, e.g., murine, origin), and/or single chain. Both polyclonal and monospecific antibodies may also be in the form of immunoglobulin fragments, e.g., F(ab)'2 or Fab fragments. The antibodies of the invention are of any isotype, e.g., IgG or IgA, and polyclonal antibodies are of a single isotype or a mixture of isotypes.

Antibodies against the polypeptides, homologs or fragments of the present invention are generated by immunization of a mammal with a composition comprising said polypeptide, homolog or fragment. Such antibodies may be polyclonal or monoclonal. Methods to produce polyclonal or monoclonal antibodies are well known in the art. For a review, see "Antibodies, A Laboratory Manual, Cold Spring Harbor Laboratory, Eds. E. Harlow and D. Lane (1988), and D. E. Yelton et al., 1981. Ann. Rev. Biochem. 50:657-680. For monoclonal antibodies, see Kohler & Milstein (1975) Nature 256:495-497.

The antibodies of the invention, which are raised to a polypeptide or polypeptide derivative of the invention, are produced and identified using standard immunological assays, e.g., Western blot analysis, dot blot assay, or ELISA (see, e.g., Coligan et al., Current Protocols in Immunology (1994) John Wiley & Sons, Inc., New York, N.Y.). The antibodies are used in diagnostic methods to detect the presence of a *Chlamydia* antigen in a sample, such as a biological sample. The antibodies are also used in affinity chromatography for purifying a polypeptide or polypeptide derivative of the invention. As is discussed further below, such antibodies may be used in prophylactic and therapeutic passive immunization methods.

Accordingly, a ninth aspect of the invention provides (i) a reagent for detecting the presence of *Chlamydia* in a biological sample that contains an antibody, polypeptide, or polypeptide derivative of the invention; and (ii) a diagnostic method for detecting the presence of *Chlamydia* in a biological sample, by contacting the biological sample with an antibody, a polypeptide, or a polypeptide derivative of the invention, such that an immune complex is formed, and by detecting such complex to indicate the presence of *Chlamydia* in the sample or the organism from which the sample is derived.

Those skilled in the art will readily understand that the immune complex is formed between a component of the sample and the antibody, polypeptide, or polypeptide derivative, whichever is used, and that any unbound material is removed prior to detecting the complex. It is understood that a polypeptide reagent is useful for detecting the presence of anti-*Chlamydia* antibodies in a sample, e.g., a blood sample, while an antibody of the invention is used for screening a sample, such as a gastric extract or biopsy, for the presence of *Chlamydia* polypeptides.

For diagnostic applications, the reagent (i.e., the antibody, polypeptide, or polypeptide derivative of the invention) is either in a free state or immobilized on a solid support, such as a tube, a bead, or any other conventional support used in the field. Immobilization is achieved using direct or indirect means. Direct means include passive adsorption (non-covalent binding) or covalent binding between the support and the reagent. By "indirect means" is meant that an anti-reagent compound that interacts with a reagent is first attached to the solid support. For example, if a polypeptide reagent is used, an antibody that binds to it can serve as an anti-reagent, provided that it binds to an epitope that is not involved in the recognition of antibodies in biological samples. Indirect means may also employ a ligand-receptor system, for example, where a molecule such as a vitamin is grafted onto the polypeptide reagent and the corresponding receptor immobilized on the solid phase. This is illustrated by the biotin-streptavidin system. Alternatively, a peptide tail is added chemically or by genetic engineering to the reagent and the grafted or fused product immobilized by passive adsorption or covalent linkage of the peptide tail.

Such diagnostic agents may be included in a kit which also comprises instructions for use. The reagent is labeled with a detection means which allows for the detection of the reagent when it is bound to its target. The detection means may be a fluorescent agent such as fluorescein isocyanate or fluorescein isothiocyanate, or an enzyme such as horse radish peroxidase or luciferase or alkaline phosphatase, or a radioactive element such as $^{125}$I or $^{51}$Cr.

Accordingly, a tenth aspect of the invention provides a process for purifying, from a biological sample, a polypeptide or polypeptide derivative of the invention, which involves carrying out antibody-based affinity chromatography with the biological sample, wherein the antibody is a monospecific antibody of the invention.

For use in a purification process of the invention, the antibody is either polyclonal or monospecific, and preferably is of the IgG type. Purified IgGs is prepared from an antiserum using standard methods (see, e.g., Coligan et al., Current Protocols in Immunology (1994) John Wiley & Sons, Inc., New York, N.Y.). Conventional chromatography supports, as well as standard methods for grafting antibodies, are described in, e.g., Antibodies: A Laboratory Manual, D. Lane, E. Harlow, Eds. (1988) and outlined below.

Briefly, a biological sample, such as an *C. pneumoniae* extract preferably in a buffer solution, is applied to a chromatography material, preferably equilibrated with the buffer used to dilute the biological sample so that the polypeptide or polypeptide derivative of the invention (i.e., the antigen) is allowed to adsorb onto the material. The chromatography material, such as a gel or a resin coupled to an antibody of the invention, is in either a batch form or a column. The unbound components are washed off and the antigen is then eluted with an appropriate elution buffer, such as a glycine buffer or a buffer containing a chaotropic agent, e.g., guanidine HCl, or high salt concentration (e.g., 3 M $MgCl_2$). Eluted fractions are recovered and the presence of the antigen is detected, e.g., by measuring the absorbance at 280 nm.

An eleventh aspect of the invention provides (i) a composition of matter comprising a monospecific antibody of the invention, together with a diluent or carrier; (ii) a pharmaceutical composition comprising a therapeutically or prophylactically effective amount of a monospecific antibody of the invention, and (iii) a method for treating or preventing a *Chlamydia* (e.g., *C. trachomatis*, *C. psittaci*, *C. pneumoniae* or *C. pecorum*) infection, by administering a therapeutic or prophylactic amount of a monospecific antibody of the invention to an infected individual. Additionally, the eleventh aspect of the invention encompasses the use of a monospecific antibody of the invention in the preparation of a medicament for treating or preventing *Chlamydia* infection.

The monospecific antibody is either polyclonal or monoclonal, preferably of the IgA isotype (predominantly). In passive immunization, the antibody is administered to a mucosal surface of a mammal, e.g., the gastric mucosa, e.g., orally or intragastrically, advantageously, in the presence of a bicarbonate buffer. Alternatively, systemic administration, not requiring a bicarbonate buffer, is carried out. A monospecific antibody of the invention is administered as a single active component or as a mixture with at least one monospecific antibody specific for a different *Chlamydia* polypeptide. The amount of antibody and the particular regimen used are readily determined by one skilled in the art. For example, daily administration of about 100 to 1,000 mg of antibodies over one week, or three doses per day of about 100 to 1,000 mg of antibodies over two or three days, are effective regimens for most purposes.

Therapeutic or prophylactic efficacy are evaluated using standard methods in the art, e.g., by measuring induction of a mucosal immune response or induction of protective and/or therapeutic immunity, using, e.g., the *C. pneumoniae* mouse model. Those skilled in the art will readily recognize that the *C. pneumoniae* strain of the model may be replaced with another *Chlamydia* strain. For example, the efficacy of DNA molecules and polypeptides from *C. pneumoniae* is preferably evaluated in a mouse model using *C. pneumoniae* strain. Protection is determined by comparing the degree of *Chlamydia* infection to that of a control group. Protection is shown when infection is reduced by comparison to the control group. Such an evaluation is made for polynucleotides, vaccine vectors, polypeptides and derivatives thereof, as well as antibodies of the invention.

Adjuvants useful in any of the vaccine compositions described above are as follows.

Adjuvants for parenteral administration include aluminum compounds, such as aluminum hydroxide, aluminum phosphate, and aluminum hydroxy phosphate. The antigen is precipitated with, or adsorbed onto, the aluminum compound according to standard protocols. Other adjuvants, such as RIBI (ImmunoChem, Hamilton, Mont.), are used in parenteral administration.

Adjuvants for mucosal administration include bacterial toxins, e.g., the cholera toxin (CT), the *E. coli* heat-labile toxin (LT), the *Clostridium difficile* toxin A and the *pertussis* toxin (PT), or combinations, subunits, toxoids, or mutants thereof such as a purified preparation of native cholera toxin subunit B (CTB). Fragments, homologs, derivatives, and fusions to any of these toxins are also suitable, provided that they retain adjuvant activity. Preferably, a mutant having reduced toxicity is used. Suitable mutants are described, e.g., in WO 95/17211 (Arg-7-Lys CT mutant), WO 96/06627 (Arg-192-Gly LT mutant), and WO 95/34323 (Arg-9-Lys and Glu-129-Gly PT mutant). Additional LT mutants that are used in the methods and compositions of the invention include, e.g., Ser-63-Lys, Ala-69Gly, Glu-110-Asp, and Glu-112-Asp mutants. Other adjuvants, such as a bacterial monophosphoryl lipid A (MPLA) of, e.g., *E. coli, Salmonella minnesota, Salmonella typhimurium*, or *Shigella flexneri*; saponins, or polylactide glycolide (PLGA) microspheres, is also be used in mucosal administration.

Adjuvants useful for both mucosal and parenteral administrations include polyphosphazene (WO 95/02415), DC-chol (3b-(N—(N',N'-dimethyl aminomethane)-carbamoyl) cholesterol; U.S. Pat. No. 5,283,185 and WO 96/14831) and QS-21 (WO 88/09336).

Any pharmaceutical composition of the invention containing a polynucleotide, a polypeptide, a polypeptide derivative, or an antibody of the invention, is manufactured in a conventional manner. In particular, it is formulated with a pharmaceutically acceptable diluent or carrier, e.g., water or a saline solution such as phosphate buffer saline. In general, a diluent or carrier is selected on the basis of the mode and route of administration, and standard pharmaceutical practice. Suitable pharmaceutical carriers or diluents, as well as pharmaceutical necessities for their use in pharmaceutical formulations, are described in *Remington's Pharmaceutical Sciences*, a standard reference text in this field and in the USP/NF.

The invention also includes methods in which *Chlamydia* infection are treated by oral administration of a *Chlamydia* polypeptide of the invention and a mucosal adjuvant, in combination with an antibiotic, an antacid, sucralfate, or a combination thereof. Examples of such compounds that can be administered with the vaccine antigen and the adjuvant are antibiotics, including, e.g., macrolides, tetracyclines, and derivatives thereof (specific examples of antibiotics that can be used include azithromycin or doxicyclin or immunomodulators such as cytokines or steroids). In addition, compounds containing more than one of the above-listed components coupled together, are used. The invention also includes compositions for carrying out these methods, i.e., compositions containing a *Chlamydia* antigen (or antigens) of the invention, an adjuvant, and one or more of the above-listed compounds, in a pharmaceutically acceptable carrier or diluent.

It has recently been shown that the 60 kDa cysteine rich membrane protein contains a sequence cross-reactive with the murine alpha-myosin heavy chain epitope M7A-alpha, an epitope conserved in humans (Bachmaier et al., Science (1999) 283:1335). This cross-reactivity is proposed to contribute to the development of cardiovascular disease, so it may be beneficial to remove this epitope, and any other epitopes cross-reactive with human antigens, from the protein if it is to be used as a vaccine. Accordingly, a further embodiment of the present invention includes the modification of the coding sequence, for example, by deletion or substitution of the nucleotides encoding the epitope from polynucleotides encoding the protein, as to improve the efficacy and safety of the protein as a vaccine. A similar approach may be appropriate for any protective antigen found to have unwanted homologies or cross-reactivities with human antigens.

Amounts of the above-listed compounds used in the methods and compositions of the invention are readily determined by one skilled in the art. Treatment/immunization schedules are also known and readily designed by one skilled in the art. For example, the non-vaccine components can be administered on days 1-14, and the vaccine antigen+adjuvant can be administered on days 7, 14, 21, and 28.

EXAMPLES

The above disclosure generally discribes the present invention. A more complete understanding can be obtained by reference to the following specific examples. These examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

Example 1

This example illustrates the preparation of a plasmid vector pCAmgp002 containing the OMP (outer membrane protein) gene.

The OMP (outer membrane protein) gene (SEQ ID No: 1) was amplified from *Chlamydia pneumoniae* genomic DNA by polymerase chain reaction (PCR) using a 5' primer (5' ATAAGAATGCGGCCGCCACCATGGACTATTC-CATCTAACTCTC 3'; SEQ ID No:3) and a 3' primer (5' GCGCCGGATCCCCTCCACAATTTTTATGAGT-AAGCC 3'; SEQ ID No:4). The 5' primer contains a Not I restriction site, a ribosome binding site, an initiation codon and a sequence at the 5' end of the OMP (outer membrane protein) coding sequence. The 3' primer includes the sequence encoding the C-terminal sequence of the OMP (outer membrane protein) and a Bam HI restriction site. The stop codon was excluded and an additional nucleotide was inserted to obtain an in-frame fusion with the Histidine tag.

After amplification, the PCR fragment was purified using QIAquick™ PCR purification kit (Qiagen) and then digested with Not I and Bam HI and cloned into the pCA-Myc-His eukaryotic expression vector describe in Example 2 (FIG. 3) with transcription under control of the human CMV promoter.

Example 2

This example illustrates the preparation of the eukaryotic expression vector pCA/Myc-His.

Figure 3:
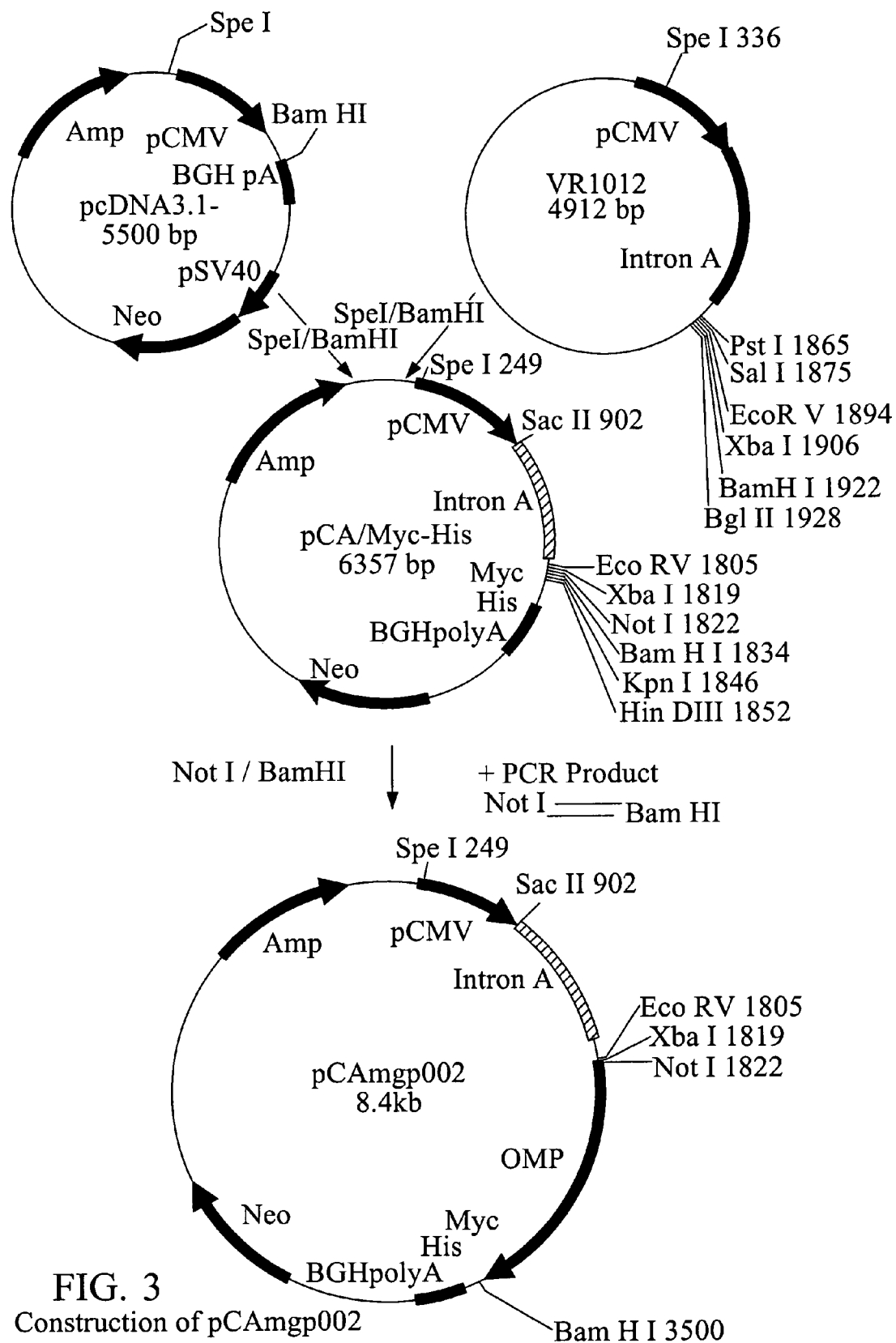
FIG. 3 shows the construction and elements of plasmid pCAmgp002.

Plasmid pcDNA3.1(−)Myc-His C (Invitrogen) was restricted with Spe I and Bam HI to remove the CMV promoter and the remaining vector fragment was isolated. The CMV promoter and intron A from plasmid VR-1012 (Vical) was isolated on a Spe I/Bam HI fragment. The fragments were ligated together to produce plasmid pCA/Myc-His. The Not I/Bam HI restricted PCR fragment containing the OMP (outer membrane protein) gene (SEQ ID No: 1) was ligated into the Not I and Bam HI restricted plasmid pCA/Myc-His to produce plasmid pCAmgp002 (FIG. 3).

The resulting plasmid, pCAmgp002, was transfered by electroporation into $E.$ $coli$ XL-1 blue (Stratagene) which was grown in LB broth containing 50 µg/ml of carbenicillin. The plasmid was isolated by Endo Free Plasmid Giga Kit™ (Qiagen) large scale DNA purification system. DNA concentration was determined by absorbance at 260 nm and the plasmid was verified after gel electrophoresis and Ethidium bromide staining and comparison to molecular weight standards. The 5' and 3' ends of the gene were verified by sequencing using a LiCor model 4000 L DNA sequencer and IRD-800 labelled primers.

Example 3

This example illustrates the immunization of mice to achieve protection against an intranasal challenge of $C.$ $pneumoniae.$ It has been previously demonstrated (Yang et. al., 1993) that mice are susceptible to intranasal infection with different isolates of $C.$ $pneumoniae$. Strain AR-39 (Grayston, 1989) was used in Balb/c mice as a challenge infection model to examine the capacity of chlamydia gene products delivered as naked DNA to elicit a protective response against a sublethal $C.$ $pneumoniae$ lung infection. Protective immunity is defined as an accelerated clearance of pulmonary infection.

Groups of 7 to 9 week old male Balb/c mice (6 to 10 per group) were immunized intramuscularly (i.m.) plus intranasally (i.n.) with plasmid DNA containing the coding sequence of $C.pneumoniae$ OMP (outer membrane protein) as described in Examples 1 and 2. Saline or the plasmid vector lacking an inserted chlamydial gene was given to groups of control animals.

For i.m. immunization, alternate left and right quadriceps were injected with 100 µg of DNA in 50 µl of PBS on three occasions at 0, 3 and 6 weeks. For i.n. immunization, anaesthetized mice aspirated 50 µl of PBS containing 50 µg DNA on three occasions at 0, 3 and 6 weeks. At week 8, immunized mice were inoculated i.n. with $5\times10^5$ IFU of $C.$ $pneumoniae$, strain AR39 in 100 µl of SPG buffer to test their ability to limit the growth of a sublethal $C.$ $pneumoniae$ challenge.

Lungs were taken from mice at day 9 post-challenge and immediately homogenised in SPG buffer (7.5% sucrose, 5 mM glutamate, 12.5 mM phosphate pH 7.5). The homogenate was stored frozen at −70° C. until assay. Dilutions of the homogenate were assayed for the presence of infectious chlamydia by inoculation onto monolayers of susceptible cells. The inoculum was centrifuged onto the cells at 3000 rpm for 1 hour, then the cells were incubated for three days at 35° C. in the presence of 1 µg/ml cycloheximide. After incubation the monolayers were fixed with formalin and methanol then immunoperoxidase stained for the presence of chlamydial inclusions using convalescent sera from rabbits infected with $C.$ $pneumoniae$ and metal-enhanced DAB as a peroxidase substrate.

FIG. 4 and Table 1 show that mice immunized i.n. and i.m. with pCAmgp002 had chlamydial lung titers less than 41,000 in 5 of 6 cases at day 9 (mean 29,783) whereas the range of values for control mice sham immunized with saline was 13,600-458,100 IFU/lung (mean 107,641) at day 9. DNA immunisation per se was not responsible for the observed protective effect since another plasmid DNA construct, pCABk917, failed to protect, with lung titers in immunised mice similar (mean 85,350 IFU/lung) to those obtained for saline-immunized control mice. The construct pCABk917 is identical to pCAmgp002 except that the nucleotide sequence encoding the OMP (outer membrane protein) is replaced with a $C.$ $pneumoniae$ nucleotide sequence encoding another hypothetical outer membrane protein based on the open reading frame.

TABLE 1

BACTERIAL LOAD (INCLUSION FORMING UNITS PER LUNG) IN THE LUNGS OF BALB/C MICE IMMUNIZED WITH VARIOUS DNA IMMUNIZATION CONSTRUCTS IMMUNIZING CONSTRUCT

| MOUSE | Saline Day 9 | pCABk917 Day 9 | pCA mgp002 Day 9 |
|---|---|---|---|
| 1 | 90000 | 72400 | 18100 |
| 2 | 69600 | 108000 | 40500 |
| 3 | 136400 | 24700 | 92700 |
| 4 | 458100 | 0 | 18600 |
| 5 | 166500 | 83600 | 5300 |
| 6 | 49500 | 223400 | 3500 |
| 7 | 13600 | | |
| 8 | 150600 | | |
| 9 | 37600 | | |
| 10 | 179700 | | |
| 11 | 91100 | | |
| 12 | 289400 | | |
| 13 | 16200 | | |
| 14 | 233300 | | |
| 15 | 36300 | | |
| 16 | 132700 | | |
| 17 | 57300 | | |
| 18 | 36900 | | |
| 19 | 115000 | | |
| 20 | 108000 | | |
| 21 | 32600 | | |
| 22 | 33400 | | |
| 23 | 16300 | | |
| 24 | 33300 | | |
| MEAN | 107641.7 | 85350 | 29783.33 |
| SD | 104011.6 | 78364.07 | 33541.52 |
| Wilcoxon p | | 0.6223 | 0.02756 |

The invention claimed is:

1. A vaccine composition comprising an isolated polypeptide consisting of the amino acid sequence set forth as SEQ ID NO:2 and a compound that facilitates delivery and/or enhance an immune response to SEQ ID NO:2.

2. The vaccine composition according to claim 1 wherein the compound is a liposome.

3. The composition according to claim 2 wherein the liposome is at least one liposome selected from the group consisting of neutral liposomes, anionic liposomes, microspheres, ISCOMS, and virus-like-particles (VLPs).

4. The composition according to claim 1 wherein the compound is an adjuvant.

5. The composition according to claim 4 which is suitable for parenteral administration.

6. The composition according to claim 5 wherein the adjuvant is at least one adjuvant selected from the group consisting of an aluminum compound, RIBI, polyphosphazene, DC-chol (3b-(N-(N',N'-dimethyl aminomethane)-carbamoyl) cholesterol and QS-21.

7. The composition according to claim 6 wherein the adjuvant is aluminum hydroxide, aluminum phosphate, or aluminum hydroxy phosphate.

8. The composition according to claim 4 which is suitable for mucosal administration.

9. The composition according to claim 8 wherein the adjuvant is at least one adjuvant selected from the group consisting of bacterial toxin, bacterial monophosphoryl lipid A (MPLA), saponin, polylactide glycolide (PLGA) microsphere, polyphosphazene, DC-chol (3b-(N-(N',N'-dimethyl aminomethane)-carbamoyl) cholesterol, and QS-21.

10. The composition according to claim 9 wherein the adjuvant is at least one bacterial toxin selected from the group consisting of cholera toxin (CT), *E. Coli* heat-labile toxin (LT), *Clostridium difficile* toxin A, *pertussis* toxin (PT), and combinations, subunits, toxoids, or mutants thereof that retain adjuvant activity and/or have reduced toxicity.

11. The composition according to claim 10 wherein the adjuvant is at least one bacterial toxin selected from the group consisting of native cholera toxin subunit B (CTB), Arg-7-Lys CT mutant, Arg-192-Gly LT mutant, Arg-9-Lys PT mutant, Glu-129-Gly PT mutant, Ser-63-Lys LT mutant, Ala-69-Gly LT mutant, Glu-110-Asp LT mutant, and Glu-112-Asp LT mutant.

12. The composition according to claim 9 wherein the adjuvant is bacterial monophosphoryl lipid A (MPLA) of *E. coli, Salmonella minnesota, Salmonella typhimurium*, or *Shigella flexneri*.

13. The composition according to claim 1 in unit dosage form.

14. The composition according to claim 2 in unit dosage form.

15. The composition according to claim 3 in unit dosage form.

16. The composition according to claim 4 in unit dosage form.

17. The composition according to claim 5 in unit dosage form.

18. The composition according to claim 6 in unit dosage form.

19. The composition according to claim 7 in unit dosage form.

20. The composition according to claim 8 in unit dosage form.

21. The composition according to claim 9 in unit dosage form.

22. The composition according to claim 10 in unit dosage form.

23. The composition according to claim 11 in unit dosage form.

24. The composition according to claim 12 in unit dosage form.

25. A vaccination kit comprising the vaccine composition as defined in claim 1 and instructions for its use in vaccinating a subject against *Chlamydia* infection.

26. A vaccination kit comprising the vaccine composition as defined in claim 2 and instructions for its use in vaccinating a subject against *Chlamydia* infection.

27. A vaccination kit comprising the vaccine composition as defined in claim 8, at least one compound selected from the group consisting of an antibiotic, an antacid, sucralfate, a cytokine immunomodulator, and instructions for using the composition and compound in vaccinating a subject against *Chlamydia* infection.

28. The kit according to claim 27 wherein the antibiotic is a macrolide, a tetracycline, or a derivative thereof.

29. The kit according to claim 27 wherein the antibiotic is azithromycin or doxicyclin, and wherein the immunomodulator is interleukin-2 (IL-2), interleukin-12 (IL-12), or a steroid.

30. A vaccination kit comprising an isolated polypeptide consisting of the amino acid set forth as SEQ ID NO:2, an adjuvant, and instructions for vaccinating a subject against *Chlamydia* infection.

31. The vaccination kit according to claim 30, wherein the adjuvant is suitable for parenteral administration and selected from the group consisting of an aluminum compound, RIBI, polyphosphazene, DC-chol (3 b-(N-(N',N'-dimethyl aminomethane)-carbamoyl) cholesterol) and QS-21, and instructions for vaccinating a subject against *Chlamydia* infection.

32. The vaccination kit according to claim 31 wherein the adjuvant is aluminum hydroxide, aluminum phosphate, or aluminum hydroxy phosphate.

33. The vaccination kit according to claim 30, wherein the adjuvant is suitable for mucosal administration and selected from the group consisting of bacterial toxin, bacterial monophosphoryl lipid A (MPLA), saponin, polylactide glycolide (PLGA) microsphere, polyphosphazene, DC-chol (3 b-(N-(N',N'-dimethyl aminomethane)-carbamoyl) cholesterol), and QS-21, and instructions for vaccinating a subject against *Chlamydia* infection.

34. The vaccination kit according to claim 33 wherein the adjuvant is at least one bacterial toxin selected from the group consisting of cholera toxin (CT), E. (previously presented) *coli* heat-labile toxin (LT), *Clostridium dfficile* toxin A, *pertussis* toxin (PT), and combinations, subunits, toxoids, or mutants thereof that retain adjuvant activity and/or have reduced toxicity.

35. The vaccination kit according to claim 34 wherein the adjuvant is at least one bacterial toxin selected from the group consisting of native cholera toxin subunit B (CTB), Arg-7-Lys CT mutant, Arg-192-Gly LT mutant, Arg-9-Lys PT mutant, Glu-129-Gly PT mutant, Ser-63-Lys LT mutant, Ala-69-Gly LT mutant, Glu- 110-Asp LT mutant, and Glu-112-Asp LT mutant.

36. The vaccination kit according to claim 33 wherein the adjuvant is bacterial monophosphoryl lipid A (MPLA) of *E. coli, Salmonella minnesota, Salmonella typhimurium*, or *Shiqella flexneri*.

* * * * *

UNITED STATES PATENT AND TRADEMARK OFFICE
CERTIFICATE OF CORRECTION

PATENT NO.        : 7,662,391 B2                                        Page 1 of 1
APPLICATION NO.   : 11/142306
DATED             : February 16, 2010
INVENTOR(S)       : Murdin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 541 days.

Signed and Sealed this

Twenty-eighth Day of December, 2010

David J. Kappos
*Director of the United States Patent and Trademark Office*